Figure 1:
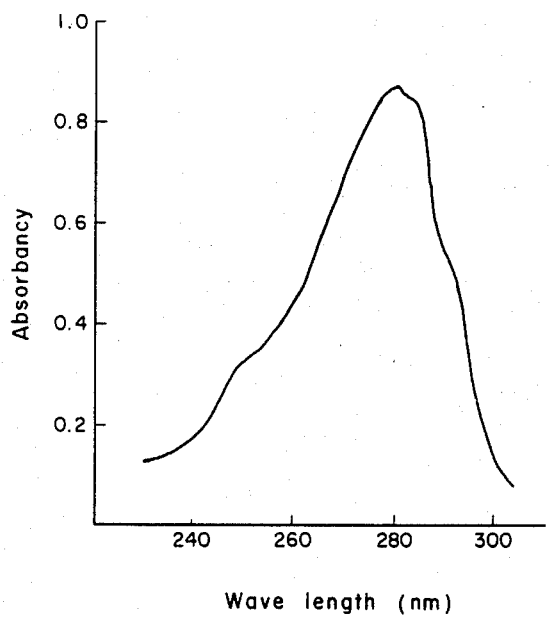

United States Patent [19]

Iwasa et al.

[11] Patent Number: 4,517,290
[45] Date of Patent: May 14, 1985

[54] METHOD FOR ENZYME IMMUNOASSAY AND PEPTIDE-ENZYME CONJUGATE AND ANTIBODY THEREFOR

[75] Inventors: Susumu Iwasa, Tsuzuki; Isamu Yoshida, Takatsuki; Koichi Kondo, Osaka, all of Japan

[73] Assignee: Takeda Chemical Industries, Ltd., Osaka, Japan

[21] Appl. No.: 533,619

[22] Filed: Sep. 19, 1983

Related U.S. Application Data

[63] Continuation of Ser. No. 244,323, Mar. 16, 1981, abandoned.

[30] Foreign Application Priority Data

Mar. 31, 1980 [JP] Japan ................................. 55-42484
Jun. 13, 1980 [JP] Japan ................................. 55-80467
Jan. 14, 1981 [JP] Japan ................................. 56-4507

[51] Int. Cl.$^3$ .................... G01N 33/54; G01N 33/56; A61K 39/395; C12N 9/96
[52] U.S. Cl. .......................................... 435/7; 424/85; 424/88; 435/188; 435/810; 436/547; 436/510; 436/814; 260/112.5 R
[58] Field of Search ........................... 435/7, 188, 810; 424/85, 88; 436/547, 510, 814; 260/112.5 R

[56] References Cited

U.S. PATENT DOCUMENTS

Re. 29,169  4/1977  Schuurs et al. ......................... 435/7
3,133,001   5/1964  Muset ................................. 435/188
4,400,316   8/1983  Katsuragi ...................... 260/112.5 R

FOREIGN PATENT DOCUMENTS 50390  12/1972  Japan .
54-895  4/1980  Japan .

OTHER PUBLICATIONS

Hurn et al., "Production of Reagent Antibodies", Methods in Enzymology, vol. 70, (1980), pp. 104, 127–130.
Roth et al., "Inactivation of Normal b-D- Galactosidase by Antibodies to Defective Formes of the Enzyme", The Journal of Biological Chemistry, vol. 250, (10-10-1975), pp. 7759–7765.
Suzuki et al., "Enzyme Activation by Antibody", The Journal of Immunology, vol. 103 (5), (1969), pp. 1366–1376.
Swaminathan et al., "Location of Major Antigenic Sites of the B Subunit of Human Chorionic Gonadotropin" Biochemistry, vol. 17 (26), (1978), pp. 5832–5838.
Fisher et al., "Synthesis of 31–and 35–Amino Acid Carboxyl Terminal Fragment of the B Subunit of the Human Chorionic Gonadotropin." Journal of Organic Chemistry, vol. 42 (21), (1977), pp. 3341–3343, C.A. 184947q.
Okada, et al., "Synthesis of C– Terminal Peptides of the Human Chorionic Gonadotropin (hCG), Chemical Pharmacology Bulletin, 28 (1), (1980), pp. 359–362, C.A. 198766v.

(List continued on next page.)

Primary Examiner—Lionel M. Shapiro
Assistant Examiner—John E. Tarcza
Attorney, Agent, or Firm—Wenderoth, Lind & Ponack

[57] ABSTRACT

In an enzyme immunoassay, when a specific antibody produced by contacting a peptide essential to the formation of a specific antibody to a peptide antigen, a freeze-dried material of β-D-galactosidase-enzyme conjugate or a peptide-enzyme conjugate prepared by coupling a labeling enzyme with a peptide of the general formula:

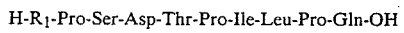

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of the peptide Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$ is used, a high reproducibility of the result of the enzyme immunoassay is obtained.

10 Claims, 12 Drawing Figures

OTHER PUBLICATIONS

Ramakrishnam et al., "Immunogenicity of Three C-Terminal Synthetic Peptides of the Beta Subunit of Human Chorionic Gonadotropin and Properties of the Antibodies raised Against 45-Acid C-Terminal Peptide", Journal of Reproductive Immunology 1 (4), (1979), pp. 249-261, C.A. 108943y.

Miles Research Products, (1976), Miles Biochemicals, Elkhart, Indiana 46514, pp. 76, 84.

Matsuura et al., "Antibodies to the Carboxyl Terminal Fragment of Human Chorionic Gonadotropin B Subunit: Characterization of Antibody Recognition Sites Using Synthetic Peptide Analogue", Biochemistry, vol. 17 (4), (1978), pp. 575-580.

Matsuura et al., "A Human Chorionic Gonadotropin-Specific Antiserum Against Synthetic Peptid Analogue to the Carboxyl-Terminal Peptide of Its B Subunit", Endocrinology, vol. 104 (2), (1979), pp. 396-401.

Kikutani et al., "Enzyme Immunoassay of Human Chorionic Gonadotropin Employing B-Galactosidase as Label", The Journal of Clinical Endocrinology and Metabolism, vol. 47 (5), (1978), pp. 980-984.

Chemical Abstracts, vol. 55, 27497, (1961).

METHOD FOR ENZYME IMMUNOASSAY AND PEPTIDE-ENZYME CONJUGATE AND ANTIBODY THEREFOR

This application is a continuation of now abandoned application Ser. No. 244,323, filed 3/16/81, now abandoned.

The present invention relates to a method for enzyme immunoassay (hereinafter sometimes referred to briefly as EIA) and a peptide-enzyme conjugate and antibody usable for EIA.

Bioassay and immunoassay are the procedures currently employed for the high-sensitivity quantitative estimation of physiologically active peptides inclusive of hormones, but bioassay has the disadvantages of complicated procedure and poor reproducibility. On the other hand, immunoassays as represented by radioimmunoassay (hereafter, sometimes briefly RIA) and enzyme immunoassay have the advantages of less complicated procedure and superior quantitative accuracy and reproducibility, but may yield variant results according to the type of antibody used and requires a scrutiny of its specificity. For example, in the quantitative estimation of human chorionic gonadotropin (hereafter, sometimes briefly hCG), its cross-reactivity with luteinizing hormone (hereafter, sometimes hLH), and in the estimation of pancreatic glucagon (hereafter, sometimes PG), its cross-reactivity with gut glucagon (hereafter, sometimes gut GLI), present problmes.

Meanwhile, the chemical analysis of these peptide hormones has made a significant step forward and an ample knowledge has by now been accumulated about the immunologically specific sites on such peptides as well as their moieties shared by certain other hormones.

Accordingly, based on such knowledge, various peptide segments are synthesized by chemical procedures and they provide immunologically specific sites of hormones which are to be quantitatively estimated, i.e. the moieties which are not shared by other hormones, and it has been found that it is possible to produce an antibody with very high specificity to the target peptide antigen by absorbing the specific antibody with such a specific peptide fragment (partial peptide).

$\beta$-D-galactosidase (hereinafter sometimes referred to briefly as $\beta$-Gal) is an enzyme which hydrolyzes lactose to galactose and glucose and is effective in the treatment of a disease caused by lactase-deficiency. More recently, its importance has further increased as a diagnostic reagent and especially as a label enzyme for EIA.

However, in solution, $\beta$-Gal is unstable regardless of whether it is alone (in unbound state) or complexed with another component (for example, an immunoactive material) and is especially unstable at low concentrations below 1 $\mu$g/ml, which is the concentration level employed in practice. Therefore, as an assay reagent, the enzyme is variable in quality and does not give reliable and consistent assay results. Furthermore, it is well known that the enzymatic activity of $\beta$-Gal tends to decrease significantly even when lyophilized.

To overcome the above disadvantages, the present inventors studied for developing a method of stabilizing $\beta$-Gal and found that the lyophilizate of an aqueous composition containing $\beta$-Gal and either a sugar or a sugar alcohol is suitable for the above purpose. This finding was followed by further studies which have resulted in the present invention.

Human chorionic gonadotropin is a proteohormone produced from chorionic cells which form on gestation, and stimulates secretion of progesterone. Detection of hCG has been commonly utilized in an early diagnosis of pregnancy. Moreover, there have recently been discovered a class of malignant tumors of hCG origin, especially a chorio-carcinoma, and hCG has been discovered in high titers in the urine, blood and spinal fluid of tumor-bearing patients. Thus, it has become clear that the qualitative and quantitative assays of this hormone are important for the diagnosis, as well as for obtaining a picture of the clinical course, of such diseases. However, such a diagnosis requires an ability to detect a trace quantity of hCG as small as about 100 IU/l, and there is also a problem involved in the immunological cross-reactivity of hCG with structurally analogous proteohormones, i.e. luteinizing hormone, follicle-stimulating hormone (hFSH) and thyroid-stimulating hormone (hTSH). Especially, since hLH closely resembles hCG and the concentration of hLH in physiological urine may at times be as high as 100 to 150 IU/l, hCG must be immunologically differentiated from hLH in order that the minute amount of hCG in a body fluid may be accurately estimated.

Meanwhile, chemical analysis of these proteohormones has made a further step forward and it has by now been elucidated that the cross-reactivity of these hormones is derived from their $\alpha$-subunits which, structurally, have a great deal in common. Therefore, an attempt has been made to separate and purify the $\beta$-subunit of hCG (hereafter briefly, hCG-$\beta$) which is comparatively distinct in structure, and prepare an anti-hCG-$\beta$ antibody using the subunit for a specific detection of hCG. However, the separation and purification of hCG-$\beta$ involves a complicated procedure and it is very difficult to prevent contamination with hCG and its $\alpha$-subunit (hereafter, hCG-$\alpha$). Because of the presence of these impurities and the amino acid sequence common to hCG and hLH, the anti-hCG-$\beta$ antibody does not completely overcome the problem of cross-reactivity between hCG and hLH. Furthermore, the affinity of this anti-hCG-$\beta$ antibody for hCG is lower than that of the anti-hCG antibody for hCG, thus causing a reduction of sensitivity.

However, the peptide moiety situated at the C-terminal of hCG-$\beta$ and consisting of about 30 amino acid residues has an amino acid sequence not shared by hLH, and it was found that this moiety permits a distinct identification of hCG versus hLH. Based on this structural analysis, Matsuura et al synthesized a C-terminal peptide of hCG-$\beta$, immunized rabbits with the peptide to obtain an hCG-specific antiserum and performed a radioimmunoassay [Endocrinology 104, p. 396, (1979)]. Though they obtained a satisfactory degree of specificity in this manner, the sensitivity of their method did not prove to be as high as desired.

Under the above technological circumstances, the present inventors conducted intensive research to develop an anti-hCG antibody that might be capable of detecting hCG with higher specificity and increased sensitivity. The present inventors immunized animals with hCG and absorbed the resultant anti-hCG antibody onto a carrier having as immobilized thereon a certain synthetic C-terminal peptide of hCG-$\beta$ to obtain an anti-hCG antibody, and found that this absorbed anti-hCG antibody is specific to hCG without showing a cross-reactivity with hLH and other proteohormones. This finding was followed by their further research which resulted in a further finding that an enzyme immunoassay employing an enzyme-labeled hCG-β C-terminal peptide is very useful for a specific and high-sensitivity detection of hCG.

The present invention is, therefore, directed to:

1. A method of producing specific antibodies, which comprises contacting a peptide essential to the formation of a specific antibody to a peptide antigen, as insolubilized on a carrier, with a body fluid containing an antibody reactive to said antigen and, then, eluting the thus-specifically absorbed antibody.

2. An enzyme immunoassay method involving the use of an antibody as a reagent, which comprises using as said antibody an antibody obtained by contacting a peptide essential to the formation of a specific antibody to a peptide antigen, as insolubilized on a carrier, with a body fluid containing an antibody reactive to said antigen and eluting the thus specifically absorbed antibody.

3. A freeze-dried material produced by freeze-drying an aqueous composition comprising β-D-galactosidase or a conjugate of β-D-galactosidase with an immunoactive material and a sugar or a sugar alcohol.

4. A method for the production of a freeze-dried material, which comprises freeze-drying an aqueous composition comprising β-D-galactosidase or a conjugate of βD-galactosidase with an immunoactive material and a sugar or a sugar alcohol.

5. A peptide-enzyme conjugate prepared by coupling a labeling enzyme with a peptide of the general formula:

H-R$_1$-Pro-Ser-Asp-Thr-Pro-Ile-Leu-Pro-Gln-OH  [I]

wherein R$_1$ is a peptide fragment consisting of 1 to 14 amino acid residues including Gly in the 14-position of the peptide Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$;

6. In a method for enzyme immunoassay of human chorionic gonadotropin involving the use of a peptide-enzyme conjugate as an assay reagent, an improvement which comprises using a peptide-enzyme conjugate prepared by coupling a labeling enzyme with a peptide of the general formula:

H-R$_1$-Pro-Ser-Asp-Thr-Pro-Ile-Leu-Pro-Gln-OH  [I]

wherein R1 is a peptide fragment consisting of 1 to 14 amino acid residues including Gly in the 14-position of the peptide Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$;

7. An assay kit for the detection of human chorionic gonadotropin, which comprises:

(1) The portion of an anti-human chorionic gonadotropin antibody which binds a given amount of the peptide-enzyme conjugate added to the reaction system, the peptide-enzyme conjugate being prepared by coupling a labeling enzyme with a peptide of the general formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of the peptide Ala$^1$Pro$^2$-Pro$^3$-Pro$^4$-Ser$^5$-Leu$^6$-Pro$^7$-Ser$^8$-Pro9-Ser$^{10}$-Arg$^{11}$-Leu$^{12}$-Pro$^{13}$-Gly$^{14}$;

(2) A given amount of the peptide-enzyme conjugate or its lyophilizate, the peptide-enzyme conjugate being prepared by coupling a labeling enzyme with a peptide of the general formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of the peptide Ala$^1$-Pro$^2$-Pro$^3$-Pro$^4$-Ser$^5$-Leu$^6$-Pro$^7$-Ser$^8$-Pro$^9$-Ser$^{10}$-Alg$^{11}$-Leu$^{12}$-Pro$^{13}$-Gly$^{14}$;

(3) From 0 to 500 IU of standard human chorionic gonadotropin;

(4) A buffer solution which is used for diluting the above reagents (1) to (3) and the sample fluid to be assayed;

(5) A given amount [sufficient to bind all of said antibody (1)] of an insoluble anti-animal immunoglobulin G-carrier conjugate;

(6) A given amount of a substrate;

(7) A buffer solution which is used for washing the second antibody-carrier conjugate (5) and dissolving the substrate (6);

(8) A buffer solution which is used for terminating the enzymatic reaction.

The method for enzyme immunoassay according to the present invention is enumerated as follows:

(1) the assay which comprises adding a known amount of a peptide-enzyme conjugate and a known amount of an insoluble form of antibody to a sample fluid containing an unknown amount of antigen and measuring the enzymatic activity of the peptide-enzyme conjugate in the liquid phase or of the reacted peptide-enzyme conjugate in the solid phase to estimate the amount of antigen in the sample fluid [FEBS Letters 15, p. 232(1971)];

(2) the assay which comprises adding a known amount of a peptide-enzyme conjugate and a known amount of a soluble form of antibody to an antigen-containing sample fluid to effect a competitive binding reaction, then adding a known amount of a second antibody insoluble with respect to the first antibody [for example, when the anti-body was prepared from rabbit serum, the anti-rabbit immunoglobulin G (IgG) antibody] and in the same manner as above in (1), measuring the enzymatic activity in the liquid phase or solid phase to estimate the quantity of antigen in the sample fluid [FEBS Letters, above];

(3) the assay which comprises adding a known amount of a peptide-enzyme conjugate and a known amount of a soluble form of antibody to an antigen-containing sample fluid to effect a competitive binding reaction in the same manner as the above assay (2), then adding a known amount of a second antibody and, when the second antibody is an anti-animal IgG antibody, a known amount of normal animal serum to cause a precipitation reaction and, in the same manner as the assay (1), measuring the enzymatic activity in the liquid phase or solid phase to estimate the quantity of hCG in the sample fluid [Clinica Chimica Acta 67, p. 283(1976)].

In any of the above-mentioned assays, it is more advantageous to measure the activity of the solid phase because the measurement of enzymatic activity in the liquid phase may suffer from an interference by the impurity in the test fluid. In terms of reproducibility and sensitivity, the "double-antibody assays", i.e. (2) and (3), are preferred because these assays require only a small amount of antibody.

The peptide antigens which are to be quantitatively estimated in accordance with the present EIA are the peptide hormones occurring in the bodies of mammalian animals and including hCG, hLH, thyroid-stimulating hormone, follicle-stimulating hormone, PG, insulin, growth hormone, etc. Among said mammalian animals are man, cattle, horse, sheep, rabbit, rat, guinea pig, dog, pig and monkey.

The sample fluid to which the EIA of the present invention can be applied may be any of such body fluids as urine, serum, spinal fluid, etc., although urine and serum, in particular, are preferred.

As the antibody used in the present EIA for the detection of other than hCG, the specific antibody obtainable by the present invention is used.

The antibody used in the EIA for the detection of hCG, may be any antibody reactive to the C-terminal peptide of hCG-$\beta$. Examples of such antibody include the conventional anti-hCG antibody, the specific anti-hCG antibody obtainable by the method of the present invention, the anti-hCG serum which is obtainable by immunization with hCG, the anti-hCG-$\beta$ serum which is obtainable by immunization with hCG-$\beta$, the anti-C-terminal peptide serum which is obtainable by immunization with the C-terminal peptide of hCG-$\beta$, and the $\gamma$-globulin fractions obtainable from those antisera.

In the production of an antibody according to the present invention, an animal is inoculated with the particular peptide antigen to first produce the antibody to said peptide antigen in the body fluid of the animal. This animal may be any species of animal other than man, such as mammalian warm-blooded animals (e.g. rabbit, sheep, rat, mouse, guinea pig, cattle, horse, pig, goat), avian species (e.g. chicken, pigeon, duck, goose, quail) and cold-blooded animals (e.g. frog).

The inoculation of such animals with a peptide antigen can be performed in the conventional manner.

Then, the body fluid containing such antibody is collected and contacted with a peptide essential to the formation of a specific antibody to the peptide antigen as insolubilized on a carrier.

The term "peptide essential to the formation of a specific antibody to the peptide antigen" means a peptide having a partial structure unique to the peptide antigen and not shared by other similar peptide hormones. As examples of such peptides, the following peptides may be mentioned:

In the production of a specific antibody to hCG, the peptide having the general formula:

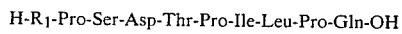

wherein $R_1$ is a peptide fragment of 1 to 14 amino acid residues including Gly in 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$Gly$^{14}$; in the production of a specific antibody to PG, the peptide having the general formula:

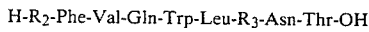

wherein $R_2$ is a peptide fragment of 1 to 10 amino acid residues including Asp in 10-position of $\beta$-Ala$^1$-Tyr$^2$-Leu$^3$-Asp$^4$-Ser$^5$-Arg$^6$-Arg$^7$-Ala$^8$-Gln$^9$-Asp$^{10}$; $R_3$ is Met or Nle (see European Patent Application Publication No. 9147); and in the production of a specific antibody to insulin, a peptide having the general formula:

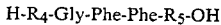

wherein $R_4$ is a peptide fragment of 1 to 3 amino acid residues including Arg in 3-position of Gly$^1$-Glu$^2$-Arg$^3$; $R_5$ is a peptide fragment of 1 to 5 amino acid residues including Tyr in 1-position of Tyr$^1$-Thr$^2$-Pro$^3$-Lys$^4$-Thr$^5$.

As examples of the peptide fragments of 1 to 14 amino acid residues including Gly in 14 position of peptide $R_1$ [i.e. Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$] is employed in the production of a specific antibody to hCG, there may be mentioned Gly, Pro-Gly, Leu-Pro-Gly, Arg-Leu-Pro-Gly, Ser-Arg-Leu-Pro-Gly, Pro-Ser-Arg-Leu-Pro-Gly, Ser-Pro-Ser-Arg-Leu-Pro-Gly, Pro-Ser-Pro-Ser-Arg-Leu-Pro-Gly, Leu-Pro-Ser-Pro-Ser-Arg-Leu-Pro-Gly, Ser-Leu-Pro-Ser-Pro-Ser-Arg-Leu-Pro-Gly, Pro-Ser-Leu-Pro-Ser-Pro-Ser-Arg-Leu-Pro-Gly, Pro-Pro-Ser-Leu-Pro-Ser- Pro-Ser-Arg-Leu-Pro-Gly, Pro-Pro-Pro-Ser-Leu-Pro-Ser-Pro-Ser-Arg-Leu-Pro-Gly, Ala-Pro-Pro-Pro-Ser-Leu-Pro Ser-Pro-Ser-Arg-Leu-Pro-Gly.

As examples of the peptide fragment of 1 to 10 amino acid residues including Asp in 10-position of $R_2$ [i.e. $\beta$-Ala$^1$-Tyr$^2$-Leu$^3$-Asp$^4$-Ser$^5$-Arg$^6$-Arg$^7$-Ala$^8$-Gln$^9$-Asp$^{10}$] which is employed in the production of a specific antibody to PG, there may be mentioned Asp, Gln-Asp, Ala-Gln-Asp, Arg-Ala-Gln-Asp, Arg-Arg-Ala-Gln-Asp, Ser-Arg-Arg-Ala-Gln-Asp, Asp-Ser-Arg-Arg-Ala-Gln-Asp, Leu-Asp-Ser-Arg-Arg-Ala-Gln-Asp, Tyr-Leu-Asp-Ser-Arg-Arg-Ala-Gln-Asp, $\beta$-Ala-Tyr-Leu-Asp-Ser-Arg-Arg-Ala-Gln-Asp.

As examples of the peptide fragment of 1 to 3 amino acid residues including Arg in 1-position of $R_4$ [Gly$^1$-Glu$^2$-Arg$^3$] which is used in the production of a specific antibody to insulin, there may be mentioned Arg, Glu-Arg and Gly-Glu-Arg. As regards the peptide fragment of 1 to 5 amino acid residues including Tyr in 1-position of $R_5$, i.e. Tyr$^1$-Thr$^2$-Pro$^3$-Lys$^4$-Thr$^5$, there may be mentioned Tyr, Tyr-Thr, Tyr-Thr-Pro, Tyr-Thr-Pro-Lys and Tyr-Thr-Pro-Lys-Thr.

The various peptides which are employed in accordance with the present invention can be produced by procedures known per se. While both of the solid-phase and the liquid-phase methods of synthesis may be employed, the latter method is more often advantageous. Such methods for peptide synthesis include those described in the literature, e.g. Schröder and Lubke: The Peptides, Vol. 1 (1966), Academic Press, New York, U.S.A. and Izumiya et al: "Peptide Gosei" (Peptide Synthesis)(1975), Maruzen Inc., Japan viz. the azide method, chloride method, acid anhydride metnod, mixed acid anhydride method, DCC method, active ester method, Woodward Reagent K method, carbodiimidazole method, reduction-oxidation method, DCC-additive (e.g. HONB, HOBt, HOSu) method and so on.

The carrier used for the production of the specific antibody according to the present invention includes, among others, beads of gels { for example, agarose gel [e. g. Sepharose 4B, Sepharose 6B (Pharmacia Fine Chemicals, Sweden)], dextran gel [e.g. Sephadex G75, Sephadex G100, Sephadex G200 (Pharmacia Fine Chemicals)], polyacrylamide gel [e.g. Biogel P30, Biogel P60, Biogel P100 (Bio-Rad Laboratories, U.S.A.]}, particles of cellulose [for example, Avicel (Asahi Kasei Inc. Japan), ion exchange cellulose (e.g. diethylaminoethyl-cellulose, carboxymethyl-cellulose)], physical adsorbents [for example, glass beads, glass rods, aminoalkyl-glass beads, aminoalkyl-glass rods), silicone rubbers, styrene resin (e.g. polystyrene beads, polystyrene granules)], ion exchange resins { for example, weakly acid cation exchange resins [e.g. Amberlite IRC-50 (Rohm and Hass, U.S.A.), Zeocarb 226 (Permutit, West Germany)], weakly basic anion exchange resins [e.g. Amberlite IR-4B (Rohm and Hass), Dowex 3 (Dow Chemical, U.S.A.)]} and so on.

Insolubilization of the peptide on such a carrier can be accomplished in the conventional manner. Among the known methods for the preparation of insolubilized peptides are those described e.g. in "Metabolism" 8 (1971) on page 696. For example, the cyanogen bromide method, GLA method, DCC method, etc. may be employed. The preferred method comprises activating the carrier with cyanogen bromide and causing the peptide to be coupled to the activated carrier.

A body fluid containing the antibody is contacted with the peptide essential to the formation of a specific antibody to the peptide antigen as insolubilized on a carrier in the following manner. Thus, for example, the body fluid is fractionally precipitated and, then, the resulting fluid, or its immunoglobulin G fraction isolated by column chromatography, is contacted with the above insolubilized peptide. The above salting-out procedure can be carried out using sodium sulfate, ammonium sulfate, magnesium sulfate, potassium phosphate, sodium citrate or the like. The above-mentioned column chromatography is carried out using, for example, diethylaminoethyl (DEAE)-cellulose, carboxymethyl (CM)-cellulose, DEAE-Sephadex, Sephadex G 150, Sephadex G 200 (Pharmacia), etc.

The elution of the specifically absorbed antibody is carried out using a buffer solution of low pH or high pH, or a buffer solution containing a high concentration of a salt, for instance.

The buffer solution of low pH may for example be a 0.17 M glycine-hydrochloric acid buffer of pH 2.3 or a 0.1 M sodium citrate-hydrochloric acid buffer of pH 1.8.

The buffer solution of high pH may for example be aqueous ammonia at pH 11 or a 0.2 M sodium borate buffer of pH 11.7.

The buffer solution containing a high concentration of a salt may for example be a 6 M guanidine hydrochloride solution or a 7 M urea solution.

The elution procedure mentioned above may be carried out batchwise or by means of a column.

The antibody-containing eluate is purfied, for example by dialysis. For example, the eluate is first neutralized, e.g. with 0.1 M sodium carbonate buffer (pH 10.5) when a buffer solution of low pH was used as an eluent or with 0.1 M glycine-hydrochloric acid buffer (pH 3.0) when the eluent was a buffer solution of high pH, and then dialyzed against e.g. 0.02 M phosphate-NaCl (pH 8.0) containing 0.1% $NaN_3$. The eluate obtained with said buffer solution containing a high concentration of NaCl can be directly dialyzed against the above phosphate-NaCl buffer and stored as such. Moreover, the above eluate or dialyzate can be freeze-dried and stored as a lyophilizate.

The specific antibody produced by the method of this invention can be used in RIA, EIA, latex and erythrocyte agglutination reactions, etc., and in any of these procedures, permits a specific detection of the target peptide antigen without interference from cross-reactive "inhibitory" peptide compounds concomitantly present in the test fluid. Especially, the application of the specific antibody of the present invention to EIA permits determinations in clinical laboratories which are not adequately equipped for the handling of radioactive isotopes and is also of value in that it ensures an expedient high-sensitivity estimation of peptide antigens in urine and blood samples.

More concretely, an anti-hCG antibody-containing body fluid obtained by immunizing an animal with hCG, especially the serum, is contacted with the insolubilized peptide of general formula [I] on the carrier. In this step, the body fluid is subjected to salting-out precipitation with e.g. sodium sulfate or ammonium sulfate, and either directly or after separation of the IgG fraction by column chromatography with DEAE-cellulose or the like, the above insolubilized peptide is contacted with the said fluid or fraction to selectively absorb the specific anti-hCG antibody onto the solid phase. By the above procedure, anti-hCG antibodies showing cross-reactivities with hLH, hFSH and hTSH can be eliminated. Then, the specific anti-hCG antibody absorbed to the solid phase is eluted. This elution is carried out with a buffer solution of low pH or high pH (for example, 0.17 M glycine-HCl buffer at pH 2.3; aqueous ammonia at pH 11) or a buffer solution containing a high concentration of a salt (for example, 6 M guanidine.hydrochloric acid solution, 7 M urea solution), whereby the specific antibody fraction is separated. Though this procedure may be carried out in a batch method, the use of a column is preferred.

When a conjugate of a peptide (I): H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH and Sepharose 4B (Pharmacia Fine Chemicals) is used in the production of the specific antibody, a highly specific anti-hCG antibody can be recovered in good yield.

The physical properties of this antibody are as follows. (1) At a final dilution of 10 to 200 ng/ml, it is capable of binding 10 to 100% of an hCG-labeling enzyme conjugate, a peptide (I)-labeling enzyme conjugate, a peptide (II)-labeling enzyme conjugate and a peptide (III)-labeling enzyme conjugate, the enzymatic activity of which is about 2 $\mu U$; (2) its optimal pH for antigen binding activity is pH 6 to 9; (3) it is stable for more than one year under refrigerator storage conditions; (4) it has a molecular weight of about 140 thousand to 170 thousand and contains about 2 to 7% of sugar; (5) it is readily soluble in aqueous medium at pH 2 to 12; (6) its electrophoretic behavior belongs to that of the γ-globulin fraction; (7) it has an ultraviolet absorption spectrum as reproduced in FIG. 1; (8) its amino acid composition in terms of the number of moles of each amino acid per 100 moles of glycine is: lysine 85 to 97, histidine 35 to 43, arginine 38 to 45, aspartic acid 110 to 132, threonine 98 to 107, serine 118 to 135, glutamic acid 138 to 145, proline 92 to 134, glycine 100, alanine 73 to 79, valine 129 to 138, methionine 2 to 10, isoleucine 28 to 37, leucine 100 to 112, tyrosine 38 to 48 and phenylalanine 55 to 68; (9) its molecule is composed of two H-chains and two L-chains as coupled by S-S bonds. The peptides (II) and (III) are obtained in Reference Examples 2 and 3.

Thus obtained specific antibody is useful as a reagent in the EIA mentioned above. In comparison with the conventional methods for the detection of peptide antigen, the enzyme immunoassay according to the present invention provides very specific results and is very instrumental in that it is free from interferences from the concomitant cross-reactive compounds in test fluids. Its sensitivity is high enough to make the method applicable to the early diagnosis and the prognostic management of chorionic tumors and other diseases. Thus, the EIA according to the present invention is practicable even in a clinical laboratory where radioactive isotopes cannot be easily utilized, and permits an expedient and specific estimation of the concentration of the desired peptide antigen in the test fluid.

The second antibody used in the EIA according to the present invention can be prepared by repeated injection of the IgG of an animal of the species used in the preparation of antibody (e.g. rabbit) into an animal of a different species (e.g. goat). The immunizing procedure may be any of those used routinely for the preparation of antibodies. As an example, about 2 mg per dose of IgG, together with Freund's complete adjuvant, is subcutaneously administered at intervals of 3 weeks for a total of about 4 times. This procedure provides a satisfactory antibody. The commercially available anti-rabbit IgG serum (goat) (Miles Laboratories, U.S.A.) may also be utilized.

The second insoluble antibody is prepared by precipitating the above anti-IgG serum with sodium sulfate or ammonium sulfate, separating the IgG fraction by DEAE-cellulose column chromatography and coupling the same to a solid phase such as a cyanogen bromide-activated cellulose or Sephadex (FEBS Letters 15, 1971, page 232). Alternatively, the above anti-serum IgG fraction may be contacted with silicon rubbers or polystyrene beads to physically adsorb the second antibody on the solid phase [Kagaku-to-Seibutsu (Chemistry and Biology) 14 (1976), p. 741].

In the present EIA, a peptide-labeling enzyme conjugate is used as one of the reagents.

The peptide in the peptide-labeling enzyme conjugate may be the very peptide antigen as such, but in order to obtain a still higher selectivity, a peptide-labeling enzyme conjugate comprising a peptide essential to the formation of a specific antibody to said peptide antigen is employed. For the quantitative estimation of hCG, for instance, it is preferable to employ a peptide-enzyme conjugate obtainable by coupling a labeling enzyme to a peptide of general formula:

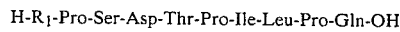
H-R₁-Pro-Ser-Asp-Thr-Pro-Ile-Leu-Pro-Gln-OH wherein R₁ is as defined hereinbefore.

For the measurement of PG it is preferable to employ a peptide-enzyme conjugate obtainable by coupling a labeling enzyme to a peptide of the general formula:

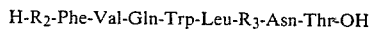
H-R₂-Phe-Val-Gln-Trp-Leu-R₃-Asn-Thr-OH wherein R₂ and R₃ are as defined hereinbefore.

When the substance to be measured is insulin, it is preferable to employ a peptide-enzyme conjugate which is obtainable by coupling a labeling enzyme to a peptide of the general formula:

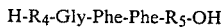
H-R₄-Gly-Phe-Phe-R₅-OH wherein R₄ and R₅ are as defined hereinbefore.

As species of R₁, R₂, R₄ and R₅, those mentioned hereinbefore by way of example are useful.

As examples of such fragment peptides and the production of the fragment peptide, there may be mentioned the corresponding fragment peptides and the corresponding method for the production of the fragment peptide as described above.

The labeling enzyme is desirably an enzyme which is stable and has a high specific activity. Thus, there may be mentioned, for example, (1) carbohydrase [for example, glycosidase (e.g. β-galactosidase, β-glucosidase, β-gluscuronidase, β-fructosidase, α-galactosidase, α-glucosidase, α-mannosidase), amylase (e.g. α-amylase, β-amylase, isoamylase, glucoamylase, Taka-amylase A), cellulase, lysozyme], (2) amidase (e.g. urease, asparaginase), (3) esterase [for example, cholinesterase (e.g. acetylcholinesterase), phosphatase (e.g. alkaline phosphatase), sulfatase, lipase], (4) nuclease (e.g. deoxyribonuclease, ribonuclease), (5) iron-porphyrin enzymes (e.g. catalase, peroxidase, cytochrome oxidase), (6) copper enzymes (e.g. tyrosinase, ascorbic acid oxidase), (7) dehydrogenase (e.g. alcohol dehydrogenase, malic acid dehydrogenase, lactic acid dehydrogenase, isocitric acid dehydrogenase), etc.

In the production of the peptide-labeling enzyme conjugate according to the present EIA, the substitutable groups, such as amino, carboxyl, hydroxyl, sulfohydryl, etc., contained in the amino acid units of peptides and labeling enzymes can be utilized. These substituents occurring in peptides and labeling enzymes are activated on treatment with condensing agents, etc. and bind themselves to the reactive substitutable groups of the counterpart material to form cross-links.

The coupling reaction of a peptide with a labeling enzyme can be conducted in the presence of any condensing agent known to be useful for the coupling of peptides with enzymes. For example, there may be employed (1) water-soluble carbodiimide reagents such as ECDI and CMCT which are capable of effecting a dehydrative condensation of the reactive amino group of either the peptide or the enzyme with the reactive carboxyl group of the mating material in an aqueous solvent, (2) maleimido-N-hydroxysuccinimide esters such as m-MBHS and p-MCHS which induce a reaction of the reactive amino group of the peptide with the active N-hydroxysuccinimide ester to give a maleimide and, then, induce a reaction with the sulfhydryl group of the enzyme, and (3) dialdehyde reagents such as succindialdehyde and GLA which induce a binding of the reactive amino group of either the peptide or the enzyme with the reactive amino group of the other material.

The coupling reaction can be carried out in an aqueous solvent, which may be selected from among the solvents known to be usable for peptide-enzyme condensation. Examples include phosphate buffer between pH 6 and 8, borate buffer between pH 7 and 9, etc.

The reaction time of this peptide-enzyme coupling is normally 30 minutes to 20 hours, but in consideration of the stability of enzymes, a short duration of 30 minutes to 3 hours is desirable. However, when the coupling reaction is conducted at low temperature, the reaction time may safely be as long as 2 to 4 days. Usually, the reaction temperature is about 4° C. to 50° C. and preferably about 15° C. to 30° C.

Following the above coupling reaction, the resultant peptide-enzyme conjugate is purified and isolated by column chromatography using a gel medium such as Sephadex G100 or G200 (Pharmacia Fine Chemicals) or Sepharose 6B or 4B (Pharmacia Fine Chemicals).

β-D-galactosidase which is employed for the purposes of this invention, may be of any origin but it is usually preferable to employ an *Escherichia, coli*-derived β-Gal which is readily available and has high specific activity to synthetic substrates such as o-nitrophenyl-β-D-galactopyranoside and 4-methylumbelliferyl-β-D-galactopyranoside.

β-Gal may be used in isolated state or in a form conjugated with an immunoactive material. The immunoactive material may for example be any of antigens, antibodies, and haptens such as drugs. The antigens include hormones [e.g. pancreatic glucagon (PG), its fragment peptides, insulin, its fragment peptides, parathyroid hormone, calcitonin, adrenocorticoid hormones, growth hormone, human chorionic gonadotropin (hCG) and its fragment peptides, luteinizing hormone, thyroid-stimulating hormone, etc.], proteins [e.g. IgG, immunoglobulin A (IgA), immunoglobulin M (IgM), immunoglobulin E (IgE), α-fetoprotein carcinoembryonic antigen, etc.], virus antigens (e.g. rubella virus HA antigen, sendai virus HA antigen, etc.) and so on. The antibodies include, for example, the antibodies (anti-PG antibody, anti-hCG antibody, anti-IgG antibody, anti-IgM antibody, anti-IgE antibody, etc.) obtainable by immunizing mammalian animals such as rabbit, rat, guinea pig, sheep, goat, etc. or avian species such as chicken, duck, goose, etc. with haptens, which are mentioned below, in accordance with the established procedure. As said haptens. there may be mentioned steroids, vitamins, catecholamines, antibiotics and other drugs (e.g. penicillins, cephalosporins, β-adrenergic drugs, etc.), and so on.

The above-mentioned fragment peptides of hCG include peptides of the following general formula:

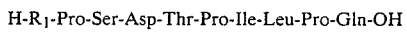
H-R$_1$-Pro-Ser-Asp-Thr-Pro-Ile-Leu-Pro-Gln-OH wherein R$_1$ has the same meaning as defined above.

The above-mentioned fragment peptides of PG include peptides of the following general formula:

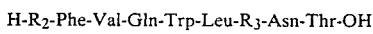
H-R$_2$-Phe-Val-Gln-Trp-Leu-R$_3$-Asn-Thr-OH wherein R$_2$ and R$_3$ have the same meaning as defined above.

The above-mentioned fragment peptides of insulin include peptides of the following general formula:

H-R$_4$-Gly-Phe-Phe-R$_5$-OH wherein R$_4$ and R$_5$ have the same meaning as defined above.

Said peptides can be produced in the manner described above.

The manner of conjugation of β-Gal with an immunoactive material may be covalent bonding. The conjugation of these components can be accomplished. for example, by the method described in Clinica Chimica Acta 81, 1 (1977); the method which comprises cross-linking the sulfhydryl group of β-Gal with the amino group of an immunoactive material with the aid of m-maleimidobenzoyl-N-hydroxysuccinimide, the method which comprises cross-linking the sulfhydryl group of β-Gal with the sulfhydryl group of an immunoactive material with the aid of 0,0-phenylenedimaleimide, the method which comprises cross-linking the amino group of β-Gal with the amino group of an immunoactive material with the aid of glutaraldehyde, and the method which comprises condensing the amino group or carboxyl group of β-Gal with the carboxyl group or amino group of an immunoactive material with the aid of carbodiimide.

As examples of the sugar employed in the practice of this invention, there may be mentioned pentoses such as arabinose, xylose, ribose, etc., hexoses such as glucose, fructose, mannose, galactose, rhamnose, etc.; disaccharides such as maltose, cellobiose, trehalose, gentiobiose, lactose, sucrose, etc.; and trisaccharides such as raffinose, maltotriose, etc. The sugar alcohol includes monosaccharides of 5 carbon atoms, e.g. xylitol, monosaccharides of 6 carbon atoms, e.g. sorbitol, mannitol, inositol, etc. Particularly preferred are arabinose, mannitol, inositol, sucrose and raffinose, and more especially desirable is sucrose. The above-mentioned sugar and sugar alcohol may be used as a mixture.

The β-Gal containing aqueous composition according to this invention may further contain albumin in addition to said sugar or/and sugar alcohol, and may still further contain magnesium or/and calcium ion donors or precursors. Allowing these additional component or components to be present in the composition helps prevent decrease of enzymatic activity in the course of lyophilization and, in the case of a conjugate of β-Gal and immunoactive material, prevent decrease of immunological activity, in addition to the effect of contributing to an improved shape of the lyophilizate. As examples of the above-mentioned albumin, there may be mentioned such serum albumins as human serum albumin, horse serum albumin, bovine serum albumin, sheep serum albumin, etc., although bovine serum albumin is preferred. The above-mentioned magnesium or/and calcium ion donors or precursors include any and all compounds capable of liberating magnesium or/and calcium ions, although magnesium salts and calcium salts may be normally employed. Preferred are magnesium chloride and calcium chloride.

In the aqueous composition of this invention, the content of β-Gal is an amount equivalent to 10 pg to 1 mg (or 0.3 microunit to 30 milliunits) per ml of the composition, and preferably 100 pg to 10 μg (or 3 microunits to 0.3 milliunit) on the same basis. The content of sugar or sugar alcohol is usually equivalent to a concentration of 0.01 to 20 w/v % in the aqueous composition and preferably 0.2 to 5 w/v % on the same basis. The content of albumin is usually equivalent to a concentration of 0.01 to 5 w/v % and preferably 0.1 to 1 w/v % in the aqueous composition. The concentration of said magnesium or/and calcium ion donors in the aqueous composition is 0.0001 to 0.1 M/l and preferably 0.0001 to 0.01 M/l.

In preparing the aqueous composition, the order of addition of the components is not critical.

The freeze-dried material according to this invention is produced by lyophilizing the above aqueous composition at about −30° C. to −50° C. and, then, removing the ice by sublimation under reduced pressure at a temperature of about 10° C. to 20° C. in the conventional manner. After this freeze-drying process, nitrogen gas sealing or vacuum sealing is preferably performed to prevent spoilage and degradation due to microorganisms such as fungi and bacteria. The nitrogen gas sealing is usually accomplished by purging the lyophilizate sufficiently with nitrogen gas and sealing it in a nitrogen gas atmosphere. The vacuum sealing is usually done by sealing the lyophilizate under reduced pressure (e.g. 10 to 0.01 mmHg).

The resultant freeze-dried material obtained by freeze-drying the aqueous composition containing β-Gal and a sugar or a sugar alcohol is very useful as an assay reagent because the enzymatic activity of β-Gal has been substantially kept intact.

The freeze-dried material obtained by freeze-drying the aqueous composition containing a β-Galimmunoactive material conjugate and a sugar or a sugar alcohol is useful as a diagnostic reagent, and because of its comparatively low price and high specific activity, is of value as a reagent for EIA. In running an EIA, an antigen-enzyme conjugate is added, along with a predetermined amount of antibody, to an antigen-containing test fluid to be assayed for a competitive binding reaction and the enzymatic activity bound or not bound to the antibody is determined.

In the estimation of hCG by the enzyme immunoassay method of the present invention, a human chorionic gonadotropin EIA kit comprising the following materials is preferably employed.

The assay kit using the second insoluble antibody comprises:

(1) The portion of an anti-human gonadotropin antibody (preferably the anti-human chorionic gonadotropin antibody prepared by the method of the present invention) which binds a given amount (preferably about 5 to 100%) of the peptide-enzyme conjugate of the present invention added to the reaction system;

(2) A given amount (preferably a portion having an enzymic activity of about 0.1 to 500 μU) of the peptideenzyme conjugate according to the present invention (which may be the lyophilizate according to the present invention);

(3) From 0 to 500 IU of standard human chorionic gonadotropin;

(4) A buffer solution (preferably a phosphate buffer of pH 6 to 9) which is used for diluting the above reagents (1) to (3) and the sample fluid to be assayed;

(5) A given amount [sufficient to bind all of first antibody (1)]of an insoluble anti-animal IgG-carrier conjugate (the carrier may be one of those mentioned herebefore);

(6) A given amount (preferably 1 to 100 μg) of a substrate;

(7) A buffer solution (preferably a phosphate buffer or carbonate buffer) which is used for washing the second antibody-carrier conjugate (5) and dissolving the substrate (6);

(8) A buffer solution (preferably a carbonate buffer or a dilute aqueous solution of sodium hydroxide) which is used for terminating the enzymatic reaction.

The above assay kit is preferably used in the following manner.

To 10-300 μl of reagent (1) are added 100-500 μl of reagent (4) and 5-100 μl of either the standard human chorionic gonadotropin (3) or the test fluid, followed by addition of 10-300 μl of reagent (2). The mixture is allowed to react at 0°-40° C. for 1 to 72 hours. Then, with the addition of a given amount of reagent (5), the system is stirred well and further reacted at 0°-40° C. for 0.5 to 24 hours. Following this reaction, the second antibody-carrier conjugate is washed with reagent (7) and, then, 10-1,000 μl of reagent (6) is added so as to initiate an enzymatic reaction. The reaction is conducted at 20°-40° C. for 0.5 to 24 hours, at the end of which time it is terminated by the addition of 1-5 ml of reagent (8). The absorbance or intensity of fluorescence of the reaction system is measured to estimate the concentration of human chorionic gonadotropin in the test fluid.

Compared with the conventional methods of producing a specific anti-hCG antibody, the method according to the present invention does not involve any complicated procedure for preparation of the immunogen, but provides a highly sensitive and specific antibody in an expedient manner.

Moreover, in comparison with the conventional methods for hCG detection, the enzyme immunoassay according to the present invention provides very specific results and is very instrumental in that it is free from interferences from the concomitant hLH, hFSH and hTSH in test fluids. Its sensitivity is high enough to make the method applicable to the early diagnosis and the prognostic management of chorio-carcinoma and other diseases. Thus, the EIA according to the present invention is practicable even in a clinical laboratory where radioactive isotopes (hereafter, briefly RI) cannot be easily utilized, and permits an expedient and specific estimation of serum hCG titers. Moreover, unlike RI-labeled peptides which have inevitable half lives, the peptide-enzyme conjugate according to the present invention is stable and can be easily produced, with the result that it can be applied successfully to a large number of test samples and provides results with high reproducibility.

Throughout this specification, when abbreviations are used for amino acids, peptides, protective groups, active groups, etc., they are either the abbreviations according to IUPAC-IUB Commission on Biological Nomenclature or the abbreviations of common use in this field of art. The following is a partial list of the abbreviations. It is to be understood that when optical isomers exist in regard to amino acids, etc., L-forms are meant unless otherwise indicated.

Ala : alanine
Pro : proline
Ser : serine
Leu : leucine
Arg : arginine
Gly : glycine
Asp : aspartic acid
Thr : threonine
Ile : isoleucine
Gln : glutamine
Glu : glutamic acid
Tyr : tyrosine
Met : methionine
Nle : norleucine
Phe : phenylalanine
Val : valine
Trp : tryptophan
Asn : Asparagine
Lys : lysine
His : histidine
Z : benzyloxycarbonyl
OBut : butyl ester
HONB : N-hydroxy-5-norbornene-2,3-dicarboximide
ONB : N-hydroxy-5-norbornene-2,3-dicarboximide ester
DMF : N,N'-dimethylformamide
DCC : N,N'-dicyclohexylcarbodiimide
DMSO : dimethylsulfoxide
THF : tetrahydrofuran
HOBt : 1-hydroxy-benzotriazole
OSu : N-hydroxysuccinimide ester
ECDI : 1-ethyl-3-(3-dimethylaminopropyl)-carbodiimide
CMCT : 1-cyclohexyl-3-(2-morpholinoethyl)-carbodiimide metho-para-toluenesulfonate
GLA : glutaraldehyde
m-MBHS : meta-maleimidobenzoyl-N-hydroxysuccinimide ester p-MCHS : para-maleimidomethylcyclohexane-1-carboxyl-N-hydroxysuccinimide ester The following examples and reference examples are merely intended to describe the present invention in further detail and should by no means be construed as limiting the scope of the invention.

In the reference examples presented below, thin layer chromatography was carried out using the silica gel plate 60F$_{254}$ from Merck and the following eluents.

Rf$^1$: chloroform-methanol=95:5
Rf$^2$: chloroform-methanol-acetic acid=9:1:0.5
Rf$^3$: ethyl acetate-pyridine-acetic acid-water=60:20:6:10
Rf$^4$: n-butanol-pyridine-acetic acid-water=30:20:6:24
Rf$^5$: ethyl acetate-n-butanol-acetic acid-water=1:1:1:1
Rf$^6$: n-butanol-acetic acid-water=12:3:5

REFERENCE EXAMPLE 1

Production of H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH [hereinafter referred to as, peptide(I)][the C-terminal fragment peptide of hCG-$\beta$ (123-145)]:

(a) Production of Z-Pro-Gln-OBu$^t$:

In 500 ml of methanol is dissolved 12.5 g of Z-Gln-OBu$^t$ and catalytic reduction is carried out with palladium black as catalyst. The catalyst is filtered off, the solvent distilled off and the residue dissolved in 300 ml of ethyl acetate. To this solution is added 200 ml of an ethyl acetate solution of Z-Pro-ONB (prepared from 9.7 g of Z-Pro-OH, 8.4 g of HONB and 8.8 g of DCC) and the mixture is stirred for 5 hours. The reaction mixture is washed with 0.2 N-HCl, 4% aqueous sodium hydrogen carbonate and water in that order, followed by drying over anhydrous sodium sulfate. The ethyl acetate is then distilled off, and the residue is crystallized by the addition of petroleum benzine and a small amount of diethyl ether and further recrystallized from the same solvent system.

Yield 13.1 g (81.5%), m.p. 86°–88° C., $[\alpha]_D^{26}$ −64.8° (c=0.5 methanol), Rf$^1$ 0.42, Rf$^2$ 0.73.
Elemental analysis (for C$_{22}$H$_{31}$O$_6$N$_3$).
Calcd. C, 60.95; H, 7.21; N, 9.69.
Found C, 61.04; H, 7.20; N, 9.49.

(b) Production of Z-Leu-Pro-Gln-OBu$^t$:

In 500 ml of methanol is dissolved 13 g of Z-Pro-Gln-OBu$^t$ and catalytic reduction is carried out in hydrogen gas streams using palladium black as catalyst. The catalyst is filtered off, the solvent distilled off and the residue dissolved in 300 ml of ethyl acetate. To this solution is added an ethyl acetate solution of Z-Leu-ONB (prepared from 7.9 g of Z-Leu-OH, 6.5 g of HONB and 6.8 g of DCC) and the mixture is stirred for 5 hours. The reaction mixture is washed with 0.2 N-HCl, 4% aqueous sodium hydrogen carbonate and water in that order, followed by drying over anhydrous sodium sulfate, and the solvent is distilled off. The residue is treated with petroleum benzine and the resulting powder is collected by filtration.

Yield 10.6 g (66.2%), m.p. 74°–77° C., $[\alpha]_D^{23}$ −81.4° (c=0.6, methanol), Rf$^1$ 0.38, Rf$^2$ 0.66
Elemental analysis (for C$_{28}$H$_{42}$O$_7$N$_4$):
Calcd. C, 61.52; H, 7.74; N, 10.25.
Found C, 61.61; H, 7.94; N, 9.92.

(c) Production of Z-Ile-Leu-Pro-Gln-OBu$^t$:

In 500 ml of methanol is dissolved 10.6 g of Z-Leu-Pro-Gln-OBu$^t$ and catalytic reduction is carried out with palladium black as catalyst. The methanol is distilled off and the residue is dissolved in 300 ml of ethyl acetate. To this solution is added 200 ml of a solution of Z-Ile-ONB (prepared from 5.1 g of Z-Ile-OH, 4.2 g of HONB and 4.4 g of DCC) in ethyl acetate-dioxane (1:1), and the mixture is stirred for 16 hours. The solvent is removed from the reaction mixture by distillation and the residue is dissolved in 400 ml of ethyl acetate. The reaction mixture is washed with 0.2 N-HCl, 4% aqueous sodium hydrogen carbonate and water in that order, followed by drying over anhydrous sodium sulfate. The solvent is distilled off, the residue treated with petroleum benzine, and the resulting powder collected by filtration.

Yield 12.1 g (94.5%), m.p. 78°–80° C. (decompn.), $[\alpha]_D^{23}$ −87.0° (c=0.42, methanol), Rf$^1$ 0.23, Rf$^2$ 0.67
Elemental analysis (for C$_{34}$H$_{53}$O$_8$N$_5$).
Calcd. C, 61.89; H, 8.10; N, 10.62.
Found C, 62.35; H, 8.31; N, 10.16.

(d) Production of Z-Pro-Ile-Leu-Pro-Gln-OBu$^t$:

In 500 ml of methanol is dissolved 12 g of Z-Ile-Leu-Pro-Gln-OBu$^t$ and catalytic reduction is carried out in hydrogen gas stream using palladium black as catalyst. The catalyst is filtered off and the solvent is distilled off. The residue is dissolved in 100 ml of DMF, 4.7 g of Z-Pro-OH and 3.0 g of HOBt are added, the mixture is cooled to 0° C., and further, 4.3 g of DCC is added. The mixture is stirred at 0° C. for 4 hours and then at room temperature for 10 hours. The precipitate is filtered off, the solvent distilled off and the residue dissolved in 400 ml of ethyl acetate. The solution is washed with 0.2 N-HCl, 4% aqueous sodium hydrogen carbonate and water in that order, followed by drying over anhydrous sodium sulfate. The solvent is distilled off, followed by addition of diethyl ether to the residue, and the mixture is warmed. After removal of the supernatant, the residue is treated with diethyl ether and the resulting powder is collected by filtration.

Yield 12.6 g (91.5%), m.p. 83°–87° C. (decompn.) $[\alpha]_D^{23}$ −121.0° (c=0.5, methanol), Rf$^1$ 0.31, Rf$^2$ 0.84
Elemental analysis (for C$_{39}$H$_{60}$O$_9$N$_6$).
Calcd. C, 61.88; H, 7.99; N, 11.10.
Found C, 62.04; H, 8.21; N, 10.70.

(e) Production of Z-Thr-Pro-Ile-Leu-Pro-Gln-OBu$^t$:

In 500 ml of methanol is dissolved 12.5 g of Z-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF. To this solution are dissolved 4.2 g of Z-Thr-OH and 2.7 g of HOBt and the solution is cooled to 0° C. Then 3.7 g of DCC is added and the mixture is stirred at 0° C. for 4 hours and at room temperature for 8 hours. The precipitate is filtered off. After removal of the solvent by distillation, the residue is extracted with 400 ml of ethyl acetate and the extract is washed with 0.2 N-HCl, 4% aqueous sodium hydrogen carbonate and water in that order, followed by drying over anhydrous sodium sulfate. The solvent is distilled off, the residue treated with diethyl ether and the resulting powder collected by filtration.

Yield 11.8 g (86.8%), m.p. 101°–105° C., $[\alpha]_D^{23}$ −124.3° (c=0.58, methanol), Rf$^1$ 0.20, Rf$^2$ 0.68
Elemental analysis (for C$_{43}$H$_{67}$O$_{11}$N$_7$):
Calcd. C, 60.19; H, 7.87; N, 11.43.
Found C, 59.54; H, 7.91; N, 11.19.

(f) Production of Z-Asp(OBu$^t$)-Thr-Pro-Ile-Leu-Pro-Gln-OBu$^t$:

In 500 ml of methanol is dissolved 11.8 g of Z-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF. To this solution are dissolved 4.5 g of Z-Asp(OBu$^t$)-OH and 2.3 g of HOBt, and the solution is cooled to 0° C. Then, 3.2 g of DCC is added, the mixture stirred at 0° C. for 4 hours and at room temperature for 10 hours, the precipitate filtered off, and the solvent distilled off. The residue is treated with 150 ml of ethyl acetate, and the resulting gel-like precipitate is collected by filtration, crystallized from ethyl acetate-diethyl ether, and collected by filtration with diethyl ether.

Yield 12.15 g (85.9%), m.p. 94°–96° C. (decompn.), $[\alpha]_D^{21}$ −109.1° (c=0.59, methanol), Rf$^1$ 0.13, Rf$^2$ 0.47

Elemental analysis (for $C_{51}H_{80}O_{14}N_8 \cdot H_2O$):

Calcd. C, 58.49; H, 7.89; N, 10.70.

Found C, 58.60; H, 8.07; N, 10.71.

(g) Production of Z-Ser-Asp(OBu$^t$)-Thr-Pro-Ile-Leu-Pro-Gln-OBu$^t$:

In 500 ml of methanol is dissolved 12 g of Z-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 100 ml of DMF, together with 2.93 g of Z-Ser-OH and 2.0 g of HOBt. The solution is cooled to 0° C., followed by addition of 2.8 g of DCC, and the mixture is stirred at 0° C. for 4 hours and then at room temperature for 12 hours. The precipitate is filtered off and the solvent is distilled off. The residue is dissolved in 500 ml of ethyl acetate. The solution is washed with 0.2 N-HCl, 4% aqueous sodium hydrogen carbonate and water in that order, followed by drying over anhydrous sodium sulfate, and the solvent is distilled off. The residue is treated with ethyl acetate and diethyl ether, and the resulting powder is collected by filtration.

Yield 11.7 g (90.0%), m.p. 111°–115° C. (decompn.), $[\alpha]_D^{21}$ −112.3° (c=0.63, methanol), Rf$^1$ 0.06, Rf$^2$ 0.31

Elemental analysis (for $C_{54}H_{85}O_{16}N_9 \cdot H_2$):

Calcd. C, 57.17; H, 7.73; N, 11.11.

Found C, 57.34; H, 7.77; N, 11.14.

(h) Production of Z-Pro-Ser-Asp(OBu$^t$)-Thr-Pro-Ile-Leu-Pro-Gln-OBu$^t$:

In 500 ml of methanol is dissolved 11.6 g of Z-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off and the solvent distilled off. The residue, together with 4.3 g of Z-Pro-OBN, is dissolved in 100 ml of DMF, and the solution is stirred at room temperature for 16 hours. The solvent is distilled off, the residue is extracted with 500 ml of ethyl acetate, and the extract is washed with 0.2 N-HCl, 4% aqueous sodium hydrogen carbonate and water in that order. After drying over anhydrous sodium sulfate, the solvent is distilled off. The residue is treated with diethyl ether and the resulting powder is collected by filtration.

Yield 11.1 g (88.1%), m.p. 117°–120° C., $[\alpha]_D^{21}$ −199.2° (c=0.61, methanol), Rf$^2$ 0.45

Elemental analysis (for $C_{59}H_{92}O_{17}N_{10} \cdot H_2O$):

Calcd. C, 57.54; H, 7.69; N, 11.38.

Found C, 57.44; H, 7.69; N, 11.38.

(i) Production of Z-Gly-Pro-Ser-Asp(OBu$^t$)-Thr-Pro-Ile-Leu-Pro-Gln-OBu$^t$:

In 500 ml of methanol is dissolved 10 g of Z-Pro-Ser-Asp(Obu$^t$)-Thr-Pro-Ile-Leu-Pro-Gln-OBu$^t$ and catalytic reduction is carried out in hydrogen gas streams using palladium black as catalyst. The catalyst is filtered off and the solvent distilled off. The residue, together with 4 g of Z-Gly-ONB, is dissolved in 80 ml of DMF, and the mixture is stirred at room temperature for 12 hours. The solvent is distilled off, the residue dissolved in 500 ml of ethyl acetate and the solution washed with 0.2 N-HCl, 4% aqueous sodium hydrogen carbonate and water in that order. After drying over anhydrous sodium sulfate, the solvent is distilled off. The residue is dissolved in 180 ml of methanol, followed by addition of 4.5 ml of hydrazine hydrate, the mixture is stirred at room temperature for 16 hours, and the solvent is distilled off. The residue is dissolved in 500 ml of ethyl acetate, the solution is washed with water, followed by drying over anhydrous sodium sulfate, and the solvent is distilled off. The residue is treated with diethyl ether and the resulting powder is collected by filtration.

Yield 7.35 g (70.2%), m.p. 131°–135° C. (decompn.), $[\alpha]_D^{22}$ −119.4° (c=0.35, methanol), Rf$^2$ 0.27

Elemental analysis (for $C_{61}H_{95}O_{18}N_{11} \cdot H_2O$):

Calcd. C, 56.86; H, 7.59; N, 11.96.

Found C, 56.65; H, 7.68; N, 12.02.

(j) Production of Z-Leu-Pro OBu$^t$:

In 800 ml of methanol is dissolved 20.2 g of Z-Pro-OBu$^t$ and catalytic reduction is carried out in hydrogen gas stream using palladium black as catalyst. The catalyst is filtered off and the solvent is distilled off. The residue is dissolved in 300 ml of ethyl acetate, followed by addition of 26.3 g of Z-Leu-OSu, and the mixture is stirred for 16 hours. The reaction mixture is washed with 0.2 N-HCl, 4% aqueous sodium hydrogen carbonate and water in that order, followed by drying over anhydrous sodium sulfate, and the solvent is distilled off to give an oily product.

Yield 27.6 g (100%), Rf$^1$ 0.71, Rf$^2$ 0.78

(k) Production of Z-Arg(NO$_2$)-Leu-Pro-OBu$^t$:

In 500 ml of methanol is dissolved 13.8 g of Z-Leu-Pro-OBu$^t$ and catalytic reduction is carried out in hydrogen gas stream using palladium black as catalyst. The catalyst is filtered off and the solvent distilled off. The residue, together with 11.7 g of Z-Arg(NO$_2$)-OH and 6.7 g of HOBt, is dissolved in 200 ml of DMF and the solution is cooled to 0° C. Then, 7.5 g of DCC is added, the mixture stirred at 0° C. for 4 hours and then at room temperature for 12 hours, the precipitate filtered off, and the solvent distilled off. The residue is extracted with 600 ml of ethyl acetate, the extract washed with 0.2 N-HCl, 4% aqueous sodium hydrogen carbonate and water in that order, followed by drying over anhydrous sodium sulfate, and the solvent is distilled off. The residue is allowed to stand and the resulting crystals are treated with diethyl ether. The residue is collected by filtration, and recrystallized from methanol.

Yield 12.4 g (60.6%), m.p. 170°–172° C., $[\alpha]_D^{26}$ −67.8° (c=0.48, methanol), Rf$^3$ 0.77

Elemental analysis (for $C_{29}H_{45}O_8N_7$):

Calcd. C, 56.20; H, 7.32; N, 15.82.

Found C, 55.79; H, 7.16; N, 15.85.

(l) Production of Z-Ser-Arg-Leu-Pro-OBu$^t$:

In 500 ml of methanol is dissolved 12.3 g of Z-Arg(NO$_2$)-Leu-Pro-OBu$^t$, followed by addition of 6.6 ml of 6 N-HCl, and catalytic reduction is carried out in hydrogen gas stream using palladium black as catalyst. The catalyst is filtered off and the solvent distilled off. The residue, together with 2.8 ml of triethylamine, is dissolved in 100 ml of DMF, and the triethylamine hydrochloride is filtered off. To the filtrate are added 4.8 g of Z-Ser-OH and 5.4 g of HONB and the mixture is cooled to 0° C. Then, 4.95 g of DCC is added, and the mixture is stirred at 0° C. for 4 hours and at room temperature for 16 hours. The precipitate is filtered off, the solvent distilled off, and the residue extracted with 500 ml of ethyl acetate. The extract is washed well with saturated aqueous sodium chloride, followed by drying over anhydrous sodium sulfate, and the solvent is distilled off to give a syrupy residue. $Rf^3$ 0.53

(m) Production of Z-Pro-Ser-Arg-Leu-Pro-OBu$^t$:

In 500 ml of methanol are dissolved 10.5 g of Z-Ser-Arg-Leu-Pro-OBu$^t$ and 3 ml of 6 N-HCl and catalytic reduction is carried out in hydrogen gas stream using palladium black as catalyst. The catalyst is filtered off, the solvent distilled off, the residue dissolved in 100 ml of DMF, and the solution neutralized with 2.52 ml of triethylamine. The triethylamine hydrochloride is filtered off, followed by addition of 8.4 g of Z-Pro-ONB, and the mixture is stirred at room temperature for 16 hours. The solvent is distilled off, 300 ml of ethyl acetate and 300 ml of saturated aqueous sodium chloride are added to the residue, and the mixture is shaken thoroughly. The reaction mixture is left standing, and oily precipitates are recovered from the aqueous layer, followed by addition of diethyl ether. The resulting powder is dissolved in methanol, the insolubles filtered off, and the solvent distilled off. The residue is further treated with diethyl ether and the resulting powder is collected by filtration.

Yield 8.45 g (70.8%), m.p. 115°–120° C. (decomp.), $[\alpha]_D^{22}$ −84.7° (c=0.53, methanol), $Rf^3$ 0.41.

Elemental analysis (for $C_{37}H_{58}O_9N_8 \cdot HCl \cdot H_2O$):
Calcd. C, 54.63; H, 7.56; N, 13.78; Cl, 4.36.
Found C, 54.50; H, 7.70; N, 14.11; Cl, 4.21.

(n) Production of Z-Ser-Pro-Ser-Arg-Leu-Pro-OBu$^t$:

In 200 ml of methanol is dissolved 3.8 g of Z-Pro-Ser-Arg-Leu-Pro-OBu$^t$ and catalytic reduction is carried out in hydrogen gas stream using palladium black as catalyst. The catalyst is filtered off, the solvent distilled off, and the residue dissolved in 30 ml of DMF. To this solution is added a solution (10 ml) of Z-Ser-ONB (prepared from 1.37 g of Z-Ser-OH, 1.24 g HONB and 1.30 g of DCC) in DMF, and the mixture is stirred at room temperature for 16 hours. The precipitate is filtered off and the solvent is distilled off. The residue is dissolved by the addition of 1 ml ethyl acetate and 1 ml of acetonitrile, then the solution is treated with ether, and the resultant powder is recovered by filtration. This powder is further dissolved in 2 ml of a 1:1 mixture of solvent $Rf^3$ and ethyl acetate, applied to a column (5.6×9.0 cm) packed with silica gel using the same solvent and developed with the same solvent. Fractions from 365 ml to 746 ml are pooled, the solvent distilled off, the residue treated with diethyl ether and the resultant powder collected by filtration.

Yield 2.12 g (50.2%), m.p. 130°–135° C. (decomp.), $[\alpha]_D^{22}$ −83.5° (c=0.38, methanol), $Rf^3$ 0.34.

Elemental analysis (for $C_{40}H_{63}O_{11}N_9 \cdot HCl \cdot H_2O$):
Calcd. C, 53.35; H, 7.39; N, 14.00; Cl, 3.94.
Found C, 53.67; H, 7.45; N, 13.72; Cl, 3.52.

(o) Production of Z-Ser-Leu-Pro-OBu$^t$:

In 700 ml of methanol is dissolved 13.8 g of Z-Leu-Pro-OBu$^t$ and catalytic reduction is carried out in hydrogen gas stream using palladium black as catalyst. The catalyst is filtered off and the solvent distilled off. The residue, together with 7.9 g of Z-Ser-OH and 8.9 g of HONB, is dissolved in 200 ml of acetonitrile and the solution is cooled to 0° C. Then, 7.5 g of DCC is added and the mixture is stirred at 0° C. for 4 hours and at room temperature for 16 hours. The precipitate is filtered off, the solvent distilled off, and the residue extracted with 500 ml of ethyl acetate. The extract is washed with 0.2 N-HCl, 4% aqueous sodium hydrogen carbonate and water in that order, followed by drying over anhydrous sodium sulfate, and the solvent is distilled off to give 17 g of oil. This oil is dissolved in 15 ml of chloroform-methanol (200:3) and applied to a column (5.4×20 cm) packed with silica gel using the same solvent and developed with the same solvent. Fractions from 1300 to 2100 ml are pooled and the solvent is distilled off to give an oily product.

Yield 12.2 g (73.1%), $Rf^1$ 0.38, $Rf^2$ 0.69

(p) Production of Z-Ser-Leu-Pro-Ser-Pro-Ser-Arg-Leu-Pro-OBu$^t$:

In 60 ml of methanol are dissolved 1.0 g of Z-Ser-Pro-Ser-Arg-Leu-Pro-OBu$^t$ and 1.2 ml of 1 N-HCl, and catalytic reduction is carried out in hydrogen gas stream using palladium black as catalyst. The catalyst is filtered off, the solvent distilled off, and the residue dissolved in 20 ml of DMF. In 7 ml of trifluoroacetic acid is dissolved 700 mg of Z-Ser-Leu-Pro-OBu$^t$ and, after 50 minutes, the solvent is distilled off. The residue is washed with a mixture of diethyl ether-petroleum ether (1:2), the washings are discarded and the oily residue is dried under reduced pressure of a vacuum pump to give a powder. The powder is immediately dissolved in the above DMF solution together with 407 mg of HONB. Then, at 0° C., 466 mg of DCC is added and the mixture stirred at 0° C. for 6 hours and then at room temperature for 16 hours. The precipitate is filtered off and the solvent distilled off. The residue is dissolved in 5 ml of solvent $Rf^3$-ethyl acetate (4:1), applied to a column (3.6×9.0 cm) packed with silica gel using the same solvent and eluted with the same solvent. Fractions from 333 to 572 ml are pooled, the solvent distilled off, the residue treated with diethyl ether, and the resulting powder is collected by filtration.

Yield 450 mg (33.8%), m.p. 110°–120° C. (decomp.), $[\alpha]_D^{24}$ −106.6° (c=0.31, methanol), $Rf^5$ 0.71

(q) Production of Z-Pro-Pro-OBu$^t$:

In 500 ml of methanol is dissolved 10.1 g of Z-Pro-OBu$^t$ and catalytic reduction is carried out in hydrogen gas stream using palladrum black as catalyst. The catalyst is filtered off and the solvent distilled off. The residue, together with 8.47 g of Z-Pro-OH and 5.4 g of HOBt, is dissolved in 300 ml of ethyl acetate, and the solution is cooled to 0° C. Then, 7.5 g of DCC is added, the mixture is stirred at 0° C. for 4 hours and then at room temperature for 12 hours, and the precipitate is filtered off. The filtrate is washed with 0.2 N-HCl, 4% aqueous sodium hydrogen carbonate and water in that order, followed by drying over anhydrous sodium sulfate, and the solvent is distilled off. The crystalline residue is treated with diethyl ether and collected by filtration.

Yield 9.85 g (74.1%), m.p. 94°–96° C., $[\alpha]_D^{22}$ −116.9° (c=0.54, methanol), $Rf^1$ 0.58, $Rf^2$ 0.72

Elemental analysis (for $C_{22}H_{30}O_5N_2$)
Calcd. C, 65.65; H, 7.51; N, 6.96.
Found C, 65.42; H, 7.38; N, 7.20.

(r) Production of Z-Pro-Pro-Pro-OBu$^t$:

In 300 ml of methanol is dissolved 9 g of Z-Pro-Pro-OBu$^t$ and catalytic reduction is carried out in hydrogen gas stream using palladium black as catalyst. The catalyst is filtered off and the solvent distilled off. The residue, together with 5.6 g of Z-Pro-OH and 3.63 g of HOBt, is dissolved in 250 ml of ethyl acetate and the solution is cooled to 0° C. Then, 5.1 g of DCC is added, and the mixture is stirred at 0° C. for 6 hours and at room temperature for 16 hours. The precipitate is filtered off. The filtrate is washed with 0.2 N-HCl, 4% aqueous sodium hydrogen carbonate and water in that order, followed by drying over anhydrous sodium sulfate, and the solvent is distilled off. The crystalline residue is treated with diethyl ether and filtered.

Yield 9.6 g (85.9%), m.p. 135°–157° C., $[\alpha]_D^{22} -176.0°$ (c=0.55, methanol), $Rf^1$ 0.40, $Rf^2$ 0.69

Elemental analysis (for $C_{27}H_{37}O_6N_3 \cdot \frac{1}{2}H_2O$):
Calcd. C, 63.76; H, 7.53; N, 8.26.
Found C, 63.77; H, 7.53; N, 8.62.

(s) Production of Z-Ala-Pro-Pro-Pro-OBu$^t$:

In 200 ml of methanol is dissolved 5 g of Z-Pro-Pro-Pro-OBu$^t$ and catalytic reduction is carried out in hydrogen gas stream using palladium black as catalyst. The catalyst is filtered off and the solvent distilled off. The residue, together with 2.23 g of Z-Ala-OH and 1.62 g of HOBt, is dissolved in 20 ml of DMF and the solution is cooled to 0° C. To this solution is added 2.27 g of DCC, and the mixture is stirred at 0° C. for 4 hours and then at room temperature for 12 hours. The precipitate is filtered off and the solvent distilled off. The residue is dissolved in 3 ml of 2% methanol-chloroform, applied to a column (3.7×10.5 cm) packed with silica gel using said solvent, and developed with said solvent. Fractions from 170 to 380 ml are pooled and the solvent is distilled off to give 4.05 g (71.0%) of oily product. $Rf^1$ 0.33, $Rf^2$ 0.67.

(t) Production of Z-Ala-Pro-Pro-Pro-Ser-Leu-Pro-Ser-Pro-Ser-Arg-Leu-Pro-OBu$^t$:

In 80 ml of methanol is dissolved 400 mg of Z-Ser-Leu-Pro-Ser-Pro-Ser-Arg-Leu-Pro-OBu$^t$ together with 0.8 ml of 1 N-HCl, and catalytic reduction is carried out in hydrogen gas stream using palladium black as catalyst. The catalyst is filtered off and the solvent is distilled off. The residue is dissolved in 10 ml of DMF, the solution neutralized with 0.11 ml of triethylamine, and the triethylamine hydrochloride is filtered off. In 2 ml of trifluoroacetic acid is dissolved 233 mg of Z-Ala-Pro-Pro-Pro-OBu$^t$ and, after 50 minutes, the solvent is distilled off. To the residue is added diethyl ether and the resulting powder is collected by filtration and dried. The powder, together with 122 mg of HONB, is dissolved in the above DMF solution and the solution is cooled to 0° C. To this solution is added 140 mg of DCC, the mixture is stirred at 0° C. for 6 hours and then at room temperature for 12 hours. The precipitate is removed by filtration, and the solvent distilled off. To the residue is added diethyl ether and the resulting powder is collected by filtration and recrystallized from acetonitrile ethyl acetate.

Yield 430 mg (82.1%), m.p. 152°–155° C. (decomp.), $[\alpha]_D^{24} -153.6°$ (c=0.45, methanol), $Rf^3$ 0.10, $Rf^5$ 0.54

Elemental analysis (for $C_{72}H_{112}O_{19}N_{16} \cdot HCl \cdot H_2O$):
Calcd. C, 55.42; H, 7.43; N, 14.37; Cl, 2.27.
Found C, 56.21; H, 7.54; N, 14.04; Cl, 2.30.

(u) Production of Z-Ala-Pro-Pro-Pro-Ser-Leu-Pro-Ser-Pro-Ser-Arg-Leu-Pro-Gly-Pro-Ser-Asp(OBu$^t$)-Thr-Pro-Ile-Leu-Pro-Gln-OBu$^t$ In 30 ml of methanol is dissolved 363 mg of Z-Gly-Pro-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off, and the residue dissolved in 10 ml of DMF. In 3 ml of trifluoroacetic acid is dissolved 430 mg of Z-Ala-Pro-Pro-Pro-Ser-Leu-Pro-Ser-Pro-Ser-Arg-Leu-Pro-OBu$^t$ and the solution is allowed to stand at room temperature for 45 minutes. The solvent is distilled off, the residue treated with diethyl ether, and the resulting powder collected by filtration and dried. The powder, together with 103 mg of HONB, is dissolved in the above DMF solution and the mixed solution is cooled to 0° C. Then, 118 mg of DCC is added and the mixture is stirred at 0° C. for 6 hours and then at room temperature for 40 hours. The precipitate is filtered off and the solvent distilled off. The residue is treated with diethyl ether and the resulting powder is collected by filtration and further reprecipitated from DMF and diethyl ether.

Yield 700 mg (95.5%), m.p. 120°–125° C. (decomp.), $[\alpha]_D^{23} -127.7°$ (c=0.12, methanol), $Rf^5$ 0.62, $Rf^6$ 0.44

Elemental analysis (for $C_{121}H_{191}O_{34}N_{27} \cdot HCl \cdot 2H_2O$):
Calcd. C, 53,12; H, 7.80; N, 14.94; Cl, 1.40.
Found C, 53.39; H, 7.62; N, 15.10; Cl, 1.54.

(v) Production of H-Ala-Pro-Pro-Pro-Ser-Leu-Pro-Ser-Pro-Ser-Arg-Leu-Pro-Gly-Pro Ser Asp-Thr-Pro-Ile-Leu-Pro Gln-OH [peptide (I)] [the C-terminal fragment peptide of hCG-β (123–145)]

In 50 ml of methanol are dissolved 580 mg of Z-Ala-Pro-Pro-Pro-Ser-Leu-Pro-Ser-Pro-Ser-Arg-Leu-Pro-Gly-Pro-Ser-Asp(OBu$^t$)-Thr-Pro-Ile-Leu-Pro-Gln-OBu$^t$ and 0.45 ml of 1 N-HCl, and catalytic reduction is carried out in hydrogen gas stream using palladium black as catalyst. The catalyst is removed by filtration, the solvent distilled off and 1 ml of water is added to the residue, followed by redistillation. The residue is dissolved in 10 ml of 90% aqueous trifluoroacetic acid and allowed to stand at room temperature for 60 minutes. After the solvent is distilled off, the residue is dissolved by addition of 10 ml of water and subjected to column chromatography on Amberlite IRA-410 (acetate-form; column size 1×5 cm). The eluate is collected. The resin is washed well with 50 ml of water and the washings are combined with the eluate and lyophilized to obtain 390 mg of a white powder. This powder is applied to a column (2×83 cm) of Sephadex LH-20 packed with 1 N-acetic acid, and developed with the same solvent. Fractions from 70 to 100 ml are pooled, lyophilized and column chromatographed in the manner as above, using said developing solvent. The fractions containing the desired compound are pooled and lyophilized to give white powder.

Yield 185 mg (35.2%), $[\alpha]_D^{23} -194.5°$ (c=0.13, 0.1 N-acetic acid), $Rf^5$ 0.06, $Rf^4$ (cellulose) 0.78.

Amino acid analysis (calcd.): Arg 1.00(1), Asp 1.00(1), Thr 1.00(1), Ser 3.74(4), Glu 1.03(1), Pro 9.59 (9), Gly 0.98(1), Ala 0.94(1), Ile 0.95(1), Leu 2.97(3). Average recovery rate: 79.3%

REFERENCE EXAMPLE 2

Production of H-Ser-Pro-Ser-Arg-Leu-Pro-Gly-Pro-Ser-Asp-Thr-Pro-Ile-Leu-Pro-Gln-OH [hereinafter referred to as peptide (II)] [the C-terminal fragment peptide of hCG-β (130–145)]

In 100 ml of methanol is dissolved 2.16 g of Z-Gly-Pro-Ser-Asp(OBu$^t$)-Thr-Pro-Ile-Leu-Pro-Gln-OBu$^t$ and catalytic reduction is carried out in hydrogen gas stream using palladium black as catalyst. The catalyst is filtered off, the solvent distilled off and the residue is dissolved in 25 ml of DMF. To this solution is added Z-Ser-Pro-Ser-Arg-Leu-Pro-OH, which has been obtained by treating 1.5 g of Z-Ser-Pro-Ser-Arg-Leu-Pro-OBu$^t$ with trifluoroacetic acid, as well as 1.22 g of HONB, followed by cooling to 0° C. Then, 701 mg of DCC is added and the mixture is stirred at 0° C. for 6 hours and at room temperature for 40 hours. The precipitate is removed by filtration and the solvent is distilled off. The residue is precipitated with ethyl acetate and diethyl ether and filtered. The precipitate is dissolved in 5 ml of solvent Rf$^3$, applied to a silica gel column (5.7×9 cm) packed with said solvent and developed also with said solvent. Fractions from 534 to 914 ml are pooled, distilled to remove the solvent, precipitated with diethyl ether and filtered.

Yield 1.1 g (33.9%), Rf$^3$ 0.20.

Then, a 70 mg portion of the above protected peptide is dissolved in 10 ml of methanol and catalytic reduction is carried out in hydrogen gas stream using palladium black as catalyst. The catalyst is filtered off and the solvent distilled off. The residue is dissolved in 1 ml of 90% trifluoroacetic acid, and after 60 minutes, the solvent is distilled off. The residue is dissolved by the addition of 3 ml of water and subjected to column chromatography on Amberlite IRA-410 (acetate-form; column size 1×1 cm), followed by lyophilization. Then, the lyophilizate is dissolved in 0.5 ml of 1 N-acetic acid, applied to a column of Sephadex LH-20 packed with 1 N-acetic acid, and developed with said solvent. The fractions containing the desired compound are pooled and lyophilized to give white powder.

Yield 22 mg (36.1%), $[\alpha]_D^{23} -159.3°$ (c=0.15, 0.1 N-acetic acid), Rf$^5$ 0.15.

Amino acid analysis (calcd.): Arg 1.01(1), Asp 1.01(1), Thr 0.98(1), Ser 2.57(3), Glu 0.96(1), Pro 4.85(5), Gly 1.00(1), Ile 0.96(1), Leu 2.04(2), average recovery rate: 81.1%.

REFERENCE EXAMPLE 3

Production of
H-Gly-Pro-Ser-Asp-Thr-Pro-Ile-Leu-Pro-Gln-OH
[hereinafter referred to as peptide (III)] [the C-terminal fragment peptide of hCG-β (136-145)]

In 2.5 ml of 90% trifluoroacetic acid is dissolved 150 mg of Z-Gly-Pro-Ser-Asp(OBu$^t$)-Thr-Pro-Ile-Leu-Pro-Gln-OBu$^t$ and the solution is allowed to stand at room temperature for 60 minutes. Then, the solvent is distilled off, the residue is dissolved in 30 ml of 50% acetic acid, and catalytic reduction is carried out in hydrogen gas stream using palladium black as catalyst. The catalyst is filtered off and the solvent is distilled off. The residue, is dissolved in 10 ml of water, subjected to column chromatography on Amberlite IRA-410 (acetate-form; column size 1×3 cm), and the resin is washed well with water. The eluate and washings are combined and lyophilized. The lyophilizate is applied to a column (2×83 cm) of Sephadex LH-20 packed with 1 N-acetic acid, and developed with said solvent. Fractions from 90 to 105 ml are pooled and lyophilized to give white powder.

Yield 70 mg (57.9%), $[\alpha]_D^{19} -150.5°$ (c=0.2, 0.1 N-acetic acid), Rf$^5$ 0.29, Rf$^4$ (cellulose) 0.55.

Amino acid analysis: Asp 1.02(1), Thr 0.98(1), Ser 0.92(1), Glu 1.04(1), Pro 3.17(3), Gly 0.99(1), Ile 0.99(1), Leu 1.00(1). Average recovery rate: 82.6%.

REFERENCE EXAMPLE 4

Production of anti-hCG antibody

In 1 ml of physiological saline was dissolved 1 mg of hCG (approx. 10,000 IU/mg) purified from the human urine by the conventional method, and 1 ml of Freund's complete adjuvant [Tachibana et al: Men-eki-no-Seikagaku (Biochemistry of Immunity), p.26, Kyoritsu Shuppan Inc. Japan (1967)] was added and stirred well to prepare an emulsion. This emulsion was injected into the bilateral femoral muscles and subcutaneously at several dorsal sites of a rabbit. The above procedure was repeated at intervals of 3 weeks for a total of 5 times and a blood sample was taken one week after the last immunization for a pilot assay. In this manner, there was obtained an anti-hCG antibody having a strong affinity for the C-terminal fragment peptide of hCG-β/enzyme conjugate.

REFERENCE EXAMPLE 5

Production of hCG-β-D-galactosidase conjugate

In 1 ml of 0.05 M phosphate buffer (pH 7.0) was dissolved 1 mg of hCG (approx. 10,000 IU/mg) and under stirring, 50 μl of THF containing 78 μg of m-MBHS was added. The mixture was allowed to react at 30° C. for 30 minutes, after which time it was immediately passed through a Sephadex G-25 column (0.9×55 cm) to remove the excess reagents. Then, elution was carried out with 0.05 M citrate buffer (pH 5.5) to isolate the maleimidated hCG. This maleimidated hCG solution (2 ml) was added dropwise to 0.5 ml of a dilute solution (1 mg/ml) of β-D-galactosidase in 0.05 M phosphate-NaCl buffer (pH 7.5) and the reaction was conducted at room temperature for 2 hours. Thereafter, the reaction mixture was passed through a column (1×15 cm) of concanavalin A-Sepharose 4B (Pharmacia Fine Chemicals) to adsorb the hCG-β-D-galactosidase conjugate. Then, elution was carried out with 0.05 M phosphate-NaCl buffer containing 0.2 M α-methylmannoside (pH 7.5) and the fractions showing both enzymatic activity and hCG-immune activity were pooled. This active eluate was further purified by Sepharose 6B column chromatography using 0.02 M phosphate-NaCl buffer (pH 7.0). The enzyme-containing fraction was separated to give an hCG-enzyme conjugate.

REFERENCE EXAMPLE 6

(1) Production of anti-hCG-β C-terminal fragment peptide (123-145) antibody

In 4 ml of 0.2 M phosphate buffer (pH 7.8) were dissolved 25 mg of the fragment peptide prepared in Reference Example 1 [hCG-β C-terminal fragment peptide (123-145)] and 50 mg of bovine thyroglobulin (briefly, BTG), followed by addition of 4 ml of a 5% aqueous solution of GLA. The mixture was stirred at room temperature for 3 hours, dialyzed against water (21×4) at 4° C., and lyophilized to give an immunogen. In 0.75 ml of physiological saline was dissolved 1.5 mg of this hCG-β C-terminal fragment peptide (123-145)-BTG conjugate and the solution was mixed well with 0.75 ml of Freund's complete adjuvant to prepare an emulsion. This emulsion was injected into the bilateral femoral muscles and subcutaneously at several dorsal sites of rabbits. The above procedure was repeated at intervals of 4 weeks for a total of 4 times and the blood was collected one week after the last immunization, and centrifuged to separate the antiserum. The above procedure provided anti-hCG-β C-terminal fragment peptide (123–145) serum F5C.

This antiserum F5C was precipitated with ammonium sulfate in the routine manner to give a γ-globulin fraction, which was then passed through a column of 2 mg hCG-conjugated Sepharose 4B (0.9 cm dia., 4 cm long).

The column was washed with 0.02 M borate buffer (pH 8.0) containing 0.15 M of NaCl, and elution was carried out with 0.17 M glycine-HCl buffer (pH 2.3), whereby an anti-hCG-β C-terminal fragment peptide (123–145) F5CS having a high affinity for hCG was obtained.

(2) Preparation of an antibody-bound solid phase

To 300 polystyrene balls (dia. 6.4 mm, Precision Plastics Ball Co., Chicago, U.S.A.) was added 50 ml of 0.01 M phosphate buffer (pH 7.7) and the mixture was warmed to 56° C. Then, 2 mg of F5CS prepared in (1) above was added and the mixture incubated at 56° C for 2 hours. It was then washed with 0.05 M phosphate buffer (pH 7.0) containing 0.1% of BSA and stored in the cold till use.

(3) Production of an anti-hCG antibody-β-Gal conjugate

In accordance with the procedure described in (1) above a rabbit was immunized with 1 mg of hCG (approx. 10,000 IU/mg) purified from human urine in the conventional manner to prepare an anti-hCG serum. This anti-hCG serum was fractionally precipitated with ammonium sulfate and subjected to affinity chromatography on a column (dia. 0.9 cm, length 4 cm) of Sepharose 4B conjugated with 5 mg of hCG-β C-terminal fragment peptide (123–145). The effluent was recovered to obtain antibody T7CS. In 2 ml of 0.05 M phosphate buffer (pH 7.0) was dissolved 4 mg of T7CS and, then, 200 μl of THF containing 400 μg of m-MBHS was added. The reaction was conducted at 30° C for 30 minutes. The reaction mixture was passed over Sephadex G-25 (column dia. 0.9 cm, length 55 cm) equilibrated with 0.02 M phosphate buffer to separate the excess reagent from the maleimidated antibody. This maleimidated antibody solution (0.5 ml) was gradually added to 0.3 ml of a diluted solution (1 mg/ml) of β-D-galactosidase in 0.02 M phosphate-NaCl buffer (pH 7.5) and the reaction was conducted at 5° C. overnight, with occasional shaking. Following the reaction, the mixture was purified by column chromatography on Sepharose 6B with 0.02 M-phosphate-NaCl buffer (pH 7.0) and the fraction containing enzyme and antibody activities were collected. The above procedure provided a conjugate of anti-hCG antibody and β-Gal.

EXAMPLE 1

Production of specific anti-hCG antibody

Five (5) grams of peptide (I) obtained in Reference Example 1 was dissolved in 8 ml of 0.1 M NaHCO₃ containing 0.5 M NaCl. To this solution was added 1 g of BrCN-activated Sepharose 4B (Pharmacia Fine Chemicals) previously washed with 1/1,000 N-HCl. The mixture was stirred at 5° C. overnight. Then, the Sepharose was washed well with the 0.1 M NaHCO₃ solution containing 0.5 M NaCl as used above, followed by addition of 10 ml of 0.5 M ethanolamine adjusted to pH 8 with hydrochloric acid. The reaction was conducted at room temperature for one hour, after wihch time the Sepharose was washed with (1) 0.1 M acetate buffer containing 1 M NaCl (pH 4.0), (2) 0.1 M borate buffer containing 1 M NaCl (pH 8.0) and (3) 0.02 M borate buffer containing 0.15 M NaCl (pH 8.0) in the order mentioned. The Sepharose was then packed into a column.

Eight (8) ml of the anti-hCG serum obtained according to Reference Example 4 was subjected to fractional precipitation with 1.5 g of anhydrous sodium sulfate and the resultant γ-globulin fraction was passed through the above column of peptide (I)-Sepharose 4B (column size: 0.9×4 cm).

The column was washed with 0.02 M borate buffer containing 0.15 M NaCl (pH 8.0) to remove the anti-hCG antibodies showing cross-reactivity with hLH, hFSH and hTSH. Then, elution was carried out with 0.17 M glycine-HCl buffer (pH 2.3) to recover the specific anti-hCG antibody having a strong affinity for the C-terminal fragment peptide of hCG-β. (Protein content 1.8 mg).

The physical properties of specific antibody thus obtained are as follows.

(1) At the final dilution of 80 ng/ml, this antibody is capable of binding about 95% of the hCG-labeling enzyme conjugate having about 2 μU of enzymatic activity and about 35% of peptide(II)-labeling enzyme conjugate having the same activity.

(2) The optimal pH range of the antigen-binding activity of this antibody is 6 to 9.

(3) When stored under refrigerator storage conditions, this antibody remains stable for more than one year.

(4) This antibody has a molecular weight of about 150 thousand and contains about 3% of sugar.

(5) It is readily soluble in aqueous medium between pH 2 and pH 12.

(6) Its electrophoretic behavior belongs to that of the γ-globulin fraction, showing a migration toward the cathode.

(7) FIG. 1 is ultraviolet absorption spectrum of the specific antibody (the absorption max: about 280 nm).

(8) The amino acid analysis of this antibody is shown in Table 1.

(9) Other properties of this antibody are identical with those of immunoglobulin G [Kikuchi et al: Ika Meneki Gaku (Medical Immunology), p. 61, Nankodo Inc. Japan (1976)].

TABLE 1

| Amino acid | The number of moles of each amino acid of antibody per 100 moles of glycine. |
|---|---|
| Lys | 94 |
| His | 40 |
| Arg | 41 |
| Asp | 114 |
| Thr | 103 |
| Ser | 126 |
| Glu | 142 |
| Pro | 103 |
| Gly | 100 |
| Ala | 77 |
| Val | 134 |
| Met | 3 |
| Ile | 33 |
| Leu | 109 |
| Tyr | 40 |
| Phe | 59 |

EXAMPLE 2

Production of peptide(I)-β-galactosidase conjugate

Peptide(I) prepared in Reference Example 1 (2.3 mg) was dissolved in a mixture of 0.5 ml of 0.05 M phosphate buffer (pH 7.0) and 0.5 ml of DMSO, followed by addition of 50 μl of THF containing 780 μg of m-MBHS. The mixture was reacted at 30° C. for 30 minutes. The reaction mixture was passed through a Sephadex G-15 column (0.9×55 cm) equilibrated with 0.02M phosphate buffer to separate the excess reagents from the maleimidated peptide. This maleimidated peptide solution (0.5 ml) was added gradually to 0.5 ml of dilute β-D-galactosidase solution (1 mg/ml) in 0.02 M phosphate-NaCl buffer (pH 7.5) and the mixture was reacted at 5° C. overnight with occasional shaking.

After the reaction was completed, the mixture was purified by Sepharose 6B column chromatography using 0.02 M phosphate-NaCl buffer (pH 7.0) to separate the enzyme-containing fraction, whereby the desired peptide-enzyme conjugate was obtained.

The physical properties of peptide-enzyme conjugate thus obtained are as follows.

(1) This conjugate decomposes such synthetic substrates used in EIA as O-nitrophenyl-β-D-galactopyranoside and 4-methylumbelliferyl-β-D-galactopyranoside to liberate 0-nitrophenol and 4-methylumbelliferone, respectively.

(2) When the synthetic substrate 4-methylumbelliferyl-β-D-galactopyranoside is employed, the Michaelis constant of this conjugate is equal to that of the intact β-D-galactosidase.

(3) The optimal pH of enzymatic activity is 6.5 to 7.3.

(4) More than about 90% of this enzymatically active conjugate is reactive to anti-hCG antibody and its immunological activity, as well as its enzymatic activity, is stable for more than 4 months under refrigerator storage conditions.

(5) The molecular weight of the conjugate is about 550 thousand and its molar peptide (I) to enzyme ratio is about 7.

(6) It is readily soluble in aqueous medium between pH 5 and pH 9.

Figure 2:
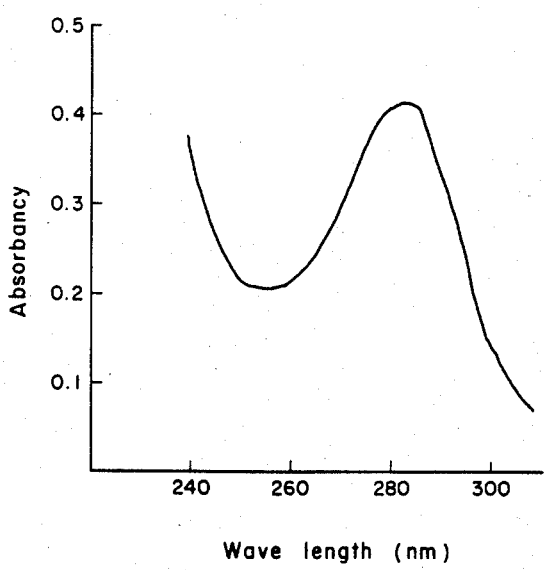

(7) FIG. 2 is ultraviolet absorption spectrum of peptide(I)-β-galactosidase conjugate (the absorption max: about 280 nm).

(8) Refer to Table 2 for the amino acid composition of the conjugate.

(9) Other properties of this conjugate are identical with those of β-D-galactosidase [Boyer: "The Enzymes", Vol. 7 (1972), p. 617, Academic Press, New York-London].

TABLE 2

| Amino acid | The number of moles of each amino acid of peptide(I)-β-D-galactosidase conjugate per 100 moles of glycine. |
|---|---|
| Lys | 31 |
| His | 51 |
| Arg | 94 |
| Asp | 153 |
| Thr | 77 |
| Ser | 80 |
| Glu | 159 |
| Pro | 99 |
| Gly | 100 |
| Ala | 109 |
| Val | 88 |
| Met | 19 |
| Ile | 60 |
| Leu | 139 |
| Tyr | 34 |
| Phe | 55 |

EXAMPLE 3

Production of peptide(II)-β-D-galactosidase conjugate

The procedure described in Example 2 was repeated except that 1.7 mg of the peptide(II) prepared in Reference Example 2 was used in place of 2.3 mg of peptide(I), whereby a peptide(II) -β-D-galactosidase was obtained.

With the exception of the following item (5), the physical properties [(1), (2), (3), (4), (6), (7), (8) and (9)] of this conjugate are identical with those of the conjugate obtained in Example 2.

(5) The molecular weight of this conjugate is about 550 thousand and its molar peptide(II)/enzyme ratio is approximately equal to 9.

EXAMPLE 4

Production of peptide(III)-β-D-galactosidase conjugate

A conjugate of peptide(III) and β-D-galactosidase was obtained by repeating the procedure of Example 2 excepting the use of 1.0 mg peptide(III) according to Reference Example 3 in lieu of 2.3 mg of peptide(I).

Excepting the following item numbered (5), physical properties of this conjugate are identical with the properties [(1), (2), (3), (4), (6), (7), (8) and (9)] of the conjugate according to Example 2.

(5) The molecular weight of the conjugate is about 550 thousand and its molar peptide(III)/enzyme ratio is approximately equal to 11.

EXAMPLE 5

Production of peptide(I)-alkaline phosphatase conjugate

In 1 ml of a dilute solution of alkaline phosphatase (0.5 mg/ml) in 0.1 M phosphate buffer (pH 6.8) was dissolved 1.2 mg of peptide(I) prepared in Reference Example 1, followed by addition of 0.1 ml of a 2% solution of GLA. The mixture was allowed to react at room temperature for 60 minutes, after which time it was dialyzed against 0.02 M phosphate-NaCl buffer (pH 6.8) at about 5° C. overnight. Then, the enzyme-containing fraction was separated by chromatographic purification on a Sephadex G-100 column using the phosphate-NaCl buffer solution (pH 6.8), whereby the desired peptide-enzyme conjugate was obtained.

The physical properties of this conjugate are as follows.

(1) This conjugate decomposes phenylphosphoric acid and p-nitrophenylphosphoric acid, both of which are synthetic substrates used in EIA, to liberate phenol and p-nitrophenol, respectively.

(2) The optimal pH range of its enzymatic activity is pH 9.3 to 10.2.

(3) More than about 90% of this enzymatically active conjugate is reactive to anti-hCG antibody, and its immunologic activity, as well as its enzymatic activity, is stable for more than 3 months under refrigerator storage conditions.

(4) It has a molecular weight of about 130 thousand and its molar peptide(I)/enzyme ratio is approximately equal to 13.

(5) It is readily soluble in aqueous medium between pH 6 and pH 11.

Figure 3:
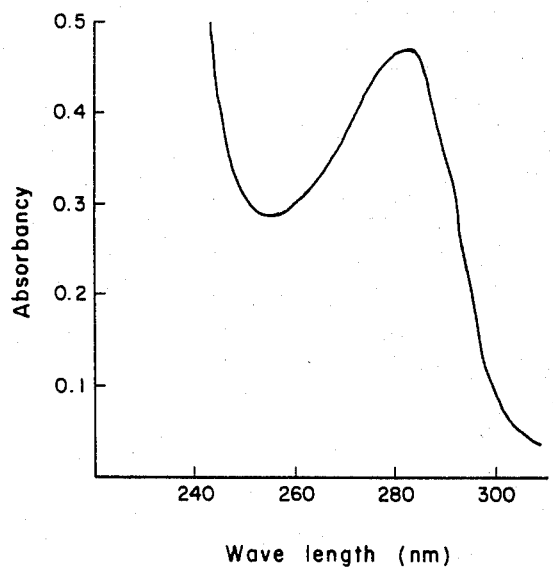

(6) FIG. 3 is ultraviolet absorption spectrum of peptide(I)-alkaline phosphatase conjugate (the absorption max: about 280 nm).

(7) Its amino acid composition is presented in Table 3.

(8) Other properties of this conjugate are identical with those of alkaline phosphatase (Boyer: "The Enzymes", Vol. 4 (1971), p. 417, Academic Press, New York-London].

TABLE 3

| Amino acid | The number of moles of each amino acid of peptide(I)-alkaline phosphatase conjugate per 100 moles of glycine. |
| --- | --- |
| Lys | 49 |
| His | 23 |
| Arg | 63 |
| Asp | 109 |
| Thr | 70 |
| Ser | 81 |
| Glu | 123 |
| Pro | 83 |
| Gly | 100 |
| Ala | 125 |
| Val | 82 |
| Met | — |
| Ile | 51 |
| Leu | 92 |
| Tyr | 32 |
| Phe | 33 |

EXAMPLE 6

Production of peptide(II)-alkaline phosphatase conjugate

A conjugate of peptide(II) and alkaline phosphatase was produced by repeating the procedure of Example 5 except that 0.83 mg of peptide(II) prepared in Reference Example 2 was used in place of 1.2 mg of peptide(I).

Excepting the following item numbered (4), physical properties of this conjugate are identical with the properties of [(1), (2), (3), (5), (6), (7) and (8)] of the conjugate according to Example 5.

(4) The molecular weight of this conjugate is about 120 thousand and its molar peptide(II)/enzyme ratio is approbimately equal to 11.

EXAMPLE 7

Production of peptide(III)-alkaline phosphatase conjugate

A conjugate of peptide(III) and alkaline phosphatase was produced by repeating the procedure of Example 5 except that 0.49 mg of peptide(III) prepared in Reference Example 3 was used in lieu of 1.2 mg of peptide(I).

Excepting the following item numbered (4), physical properties of this conjugate are identical with the properties [(1), (2), (3), (5), (6), (7) and (8)] of the conjugate according to Example 5.

(4) The molecular weight of this conjugate is about 120 thousand and its molar peptide(III)/enzyme ratio is approximately equal to 17.

EXAMPLE 8

EIA of hCG

In a preliminary assay, a mixture of 100 μl of a dilution of each antiserum, 100 μl of a peptide-β-D-galactosidase conjugate and 300 μl of an assay buffer (0.02 M phosphate buffer, pH 7.3, containing 0.5% human serum albumin, 0.5% ethylenediamine tetraacetate disodium. 2H₂O, 0.1% NaN₃ and 0.1 M NaCl) was maintained at 5° C. for 48 hours, whereby the enzymatically active moiety of the peptide-β-D-galactosidase conjugate [which had a predetermined appropriate enzymatic activity (approx. 20 μU/ml)] was bound to the antiserum. To this system was added 100 μl of a suspension of 2.5% anti-rabbit IgG antibody-cellulose complex, and the reaction was further conducted at 20° C. for 4 hours. This mixture was centrifuged and the sediment was washed and suspended in 500 μl of a substrate solution [a 20 μg/ml solution of 4-methylumbelliferyl-μ-D-galactopyranoside in 0.02 M phosphate buffer (pH 7.0) containing 0.1% bovine serum albumin, 0.1% NaN₃, 0.1 M NaCl and 1 mM MgCl₂]. The mixture was allowed to react at room temperature overnight. After this reaction, the fluorescence intensity of 4-methylumbelliferone liberated on decomposition of the substrate was measured at an excitation wavelength of 365 nm and a fluorescent wavelength of 450 nm.

The assay of hCG in a test fluid was carried out as follows. To a mixture of 50 μl of the test fluid and 250 μl of the assay buffer were added 100 μl of the antiserum at the above predetermined dilution level and 100 μl of the peptide-β-D-galactosidase conjugate. Thereafter, the same procedure as above was carried out.

Figure 4:
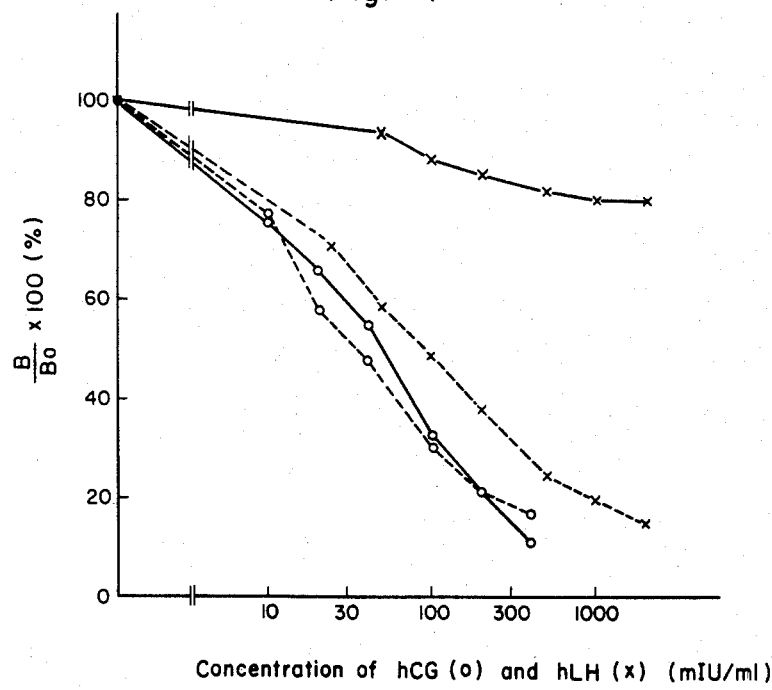
Figure 5:
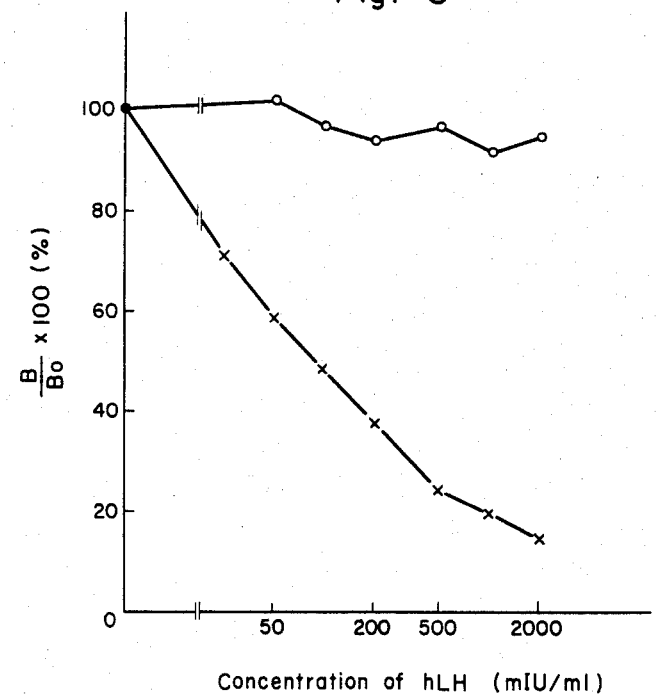

The results are set forth in FIGS. 4 and 5.

FIG. 4 is a diagram showing the standard curves of hCG(o) and hLH(x) in the EIA using the anti-hCG antibody prepared in Reference Example 4 (dotted line ---) and the specific anti-hCG antibody prepared in Example 1 (solid line —). In either system, the assay was performed using the hCG-labeling enzyme conjugate. The results indicate that while the assay system using the specific anti-hCG antibody is comparable to the system using the anti-hCG antibody in the sensitivity of hCG detection, the cross-reactivity of hLH is less than 1/1,000 as compared with hCG.

FIG. 5 shows standard curves of hLH in the EIA using the anti-hCG antibody prepared in Reference Example 4, where -o- represents the result for peptide(II) -β-D-galactosidase conjugate and -x- represents the result for the hCG-β-D-galactosidase conjugate. It is apparent that the cross-reactivity of hLH in peptide(II) -β-D-galactosidase conjugate system is very low as compared with the hCG-enzyme conjugate system.

In the FIGS. 4 and 5 as well as FIGS. 6 to 12, B indicates the enzymatic activity bound to a solid phase in the presence of the desired peptide hormone, and B₀ indicates the enzymatic activity bound to a solid phase in the absence of the desired peptide hormone.

EXAMPLE 9

EIA of hCG

As in Example 8, samples containing various dilution levels of antiserum (assay buffer 300 μl, peptide-alkaline phosphatase conjugate 100 μl and antiserum 100 μl) were allowed to stand at 5° C. for 48 hours, whereby the enzymatically active moiety of each peptide-alkaline phosphatase conjugate [which had a predetermined appropriate activity (ca. 4 mU/ml)] was bound to the antiserum. Then, 50 μl of antirabbit IgG serum (a 10-fold dilution of commercial antiserum) and 50 μl of phosphate-NaCl buffer (pH 7.5) containing 2% of normal rabbit serum were added, and the mixture was allowed to stand at 5° C. overnight. It was then centrifuged and the sediment was washed and resuspended in 500 μl of a substrate solution [2 mg/ml of p-nitrophenylphosphoric acid in 0.05 M sodium carbonate buffer containing 1 mM $MgCl_2$ (pH 9.8)]. The reaction was carried out at 37° C. overnight. Following this reaction, the absorbance of p-nitrophenol as liberated on enzymatic degradation was measured at 405 nm.

The hCG in a test fluid was assayed as follows. To a mixture of 50 μl of the test fluid and 250 μl of the assay buffer were added 100 μl of the antiserum of the dilution factor determined above and 100 μl of the peptide-alkaline phosphatase, and the assay was performed as described above. The results are shown in FIG. 6.

Figure 7:
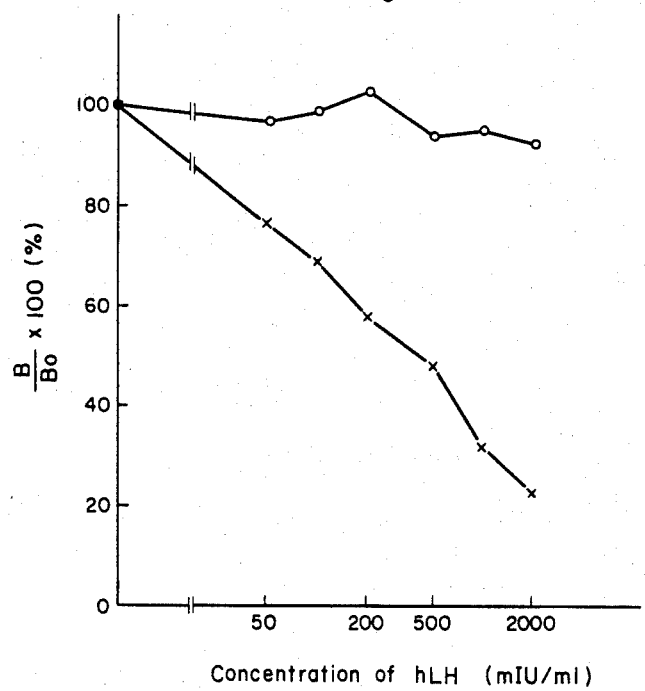

FIG. 7 is a diagram similar to FIG. 5, showing standard curves of hLH in the EIA using the anti-hCG antibody prepared in Reference Example 4, where -o- represents the result for the peptide (I)-alkaline phosphatase conjugate and -x- represents the result for the hCG-alkaline phosphatase conjugate. It is apparent that the cross-reaction of hLH is negligible in the system employin the peptide(I)-alkaline phosphatase conjugate.

Figure 6:
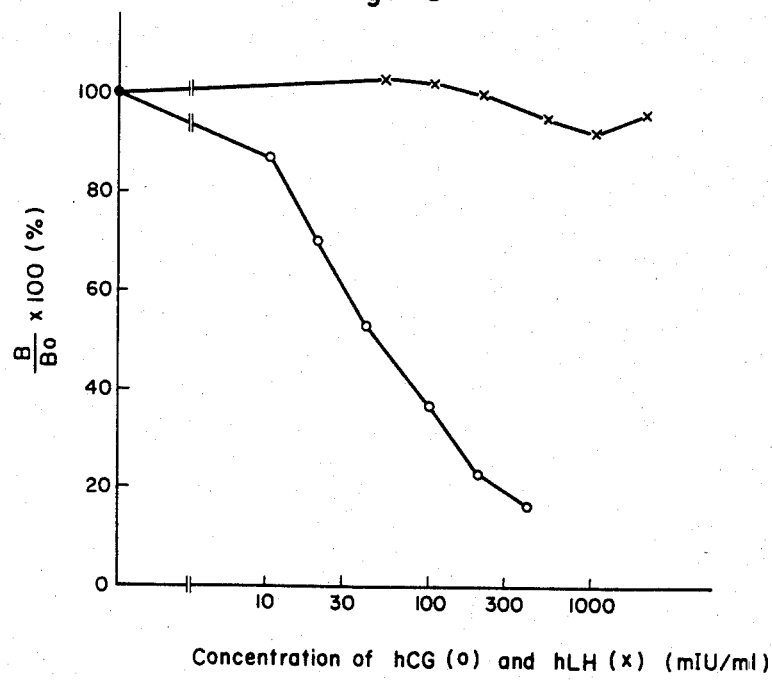

FIG. 6 shows standard curves of hCG (represented by plots -o-) and hLH (plots -x-) in the EIA using the specific anti-hCG antibody prepared in Example 1 and the peptide(II) -labeling alkaline phosphatase conjugate in combination. In this assay system, the cross-reactivity of hLH is substantially negligible. It will also be apparent that the sensitivity of hCG detection is comparable with that obtainable with the usual assay system represented by o in FIG. 4.

EXAMPLE 10

Specific enzyme immunoassay for PG (1) Preparation of anti-PG serum

In 4 ml of 0.2 M phosphate buffer (pH 7.3) were dissolved 10 mg of PG and 20 mg of bovine serum albumin (BSA), followed by addition of a 5% aqueous solution of glutaraldehyde. The mixture was stirred at room temperature for 3 hours, after which it was dialyzed against water (2 l water×4) at 4° C. and freeze-dried to give an immunogen. This PG-BSA conjugate (2 mg) was dissolved in 1 ml of physiological saline and mixed well with 1 ml of Freund's complete adjuvant to prepare an emulsion. This emulsion was injected into the both thighs and subcutaneously at several dorsal sites of the rabbit. The above procedure was repeated at intervals of 2 weeks for a total of 5 times and at one week after the last immunization a blood sample was taken for a pilot assay. In the above manner, there was obtained an anti-PG serum reactive to PG and gut GLI.

Production of a specific anti-PG antibody

In lieu of 5 mg of hCG-β C-terminal peptide described Example 1, 5 mg of PG C-terminal peptide (15–29) (H-Asp-Ser-Arg-Arg-Ala-Gln-Asp-Phe-Val-Gln-Trp-Leu-Met-Asn-Thr-OH) [See European Patent Application Publication No. 9147, Reference Example 1] was treated in the manner as Example 1 to prepare a PG C-terminal peptide (15–29)-Sepharose 4B complex.

Then, 3 ml of the anti-PG serum mentioned in (1) was salted out with anhydrous sodium sulfate and the resultant γ-globulin fraction was passed through a column (0.9×4 cm) of said C-terminal peptide (15–29)-Sepharose 4B complex.

The column was washed with 0.02 M borate buffer (pH 8.0) containing 0.15 M NaCl to eliminate the antibody crossreactive to gut GLI. Then, elution was carried out with 0.17 M glycine-hydrochloric acid buffer (pH 2.3) to give a specific anti-PG antibody (protein content 0.35 mg) having a strong affinity for the C-terminal peptide of PG.

The physical properties of this antibody are as follows. Excepting the following items numberes (1) and (8), the physical properties of the above antibody are analogous with the properties ((2), (3), (4), (5), (6), (7) and (9)) of the antibody according to Example 1.

(1) At a final dilution of 180 ng/ml, this antibody is capable of binding 53% of the PG-β-D-galactosidase conjugate [European Patent Publication No. 9147, Reference Example 9] and 18% of the PG C-terminal peptide (21-29)-β-D-galactosidase conjugate [European Patent Application Publication No. 9147, Example 3], the enzymatic activity of which is about 1 μU.

(8) Refer to Table 4 for the amino acid composition of this antibody.

(3) Assay method

In a preliminary test for each antibody-containing body fluid, a mixture of 100 μl of antiserum at a varying dilution, 100 μl of peptide-β-D-galactosidase conjugate, 50 μof Antagosan (Hoechst, 10,000 units/ml) and 250 μl of assay buffer [0.02 M phosphate buffer (pH 7.3) containing 0.5% human serum albumin (hereafter sometimes HSA), 0.5% ethylenediamine tetraacetate disodium.2H$_2$O, 0.1% NaN$_3$ and 0.1 M NaCl] was maintained at 5° C. for 96 hours, whereby the enzymatically activity of each peptide-β-D-galactosidase conjugate [which had a predetermined appropriate enzymatic activity (ca. 10 μU/ml)] was bound to the antiserum. Then, 100 μl of a 5% anti-rabbit IgG antibody-cellulose conjugate suspension was added and the reaction was further conducted at 30° C. for 4 hours. The mixture was centrifuged and the sediment was washed and suspended in 500 μl of a substrate solution [a 20 μg/ml solution of 4-methylumbelliferyl-β-D-galactopyranoside in 0.01 M phosphate buffer (pH 7.0) containing 0.1% BSA, 0.1% NaN$_3$, 0.1 M NaCl and 1 mM MgCl$_2$] and the suspension was incubated at room temperature overnight. After termination of the reaction, the intensity of fluorescence of 4-methylumbelliferone liberated on enzymatic cleavage was measured at an excitation wavelength of 365 nm and a fluorescent wavelength of 450 nm.

For the quantitative estimation of pancreatic glucagon in a test fluid, 100 μl of the antiserum of a dilution factor determined as above and 100 μl of the peptide-β-D-galactosidase conjugate were added to a mixture of 50 μl of the test fluid, 50 μl of Antagosan and 200 μl of assay buffer and an assay was carried out in the manner as described above.

Figure 8:
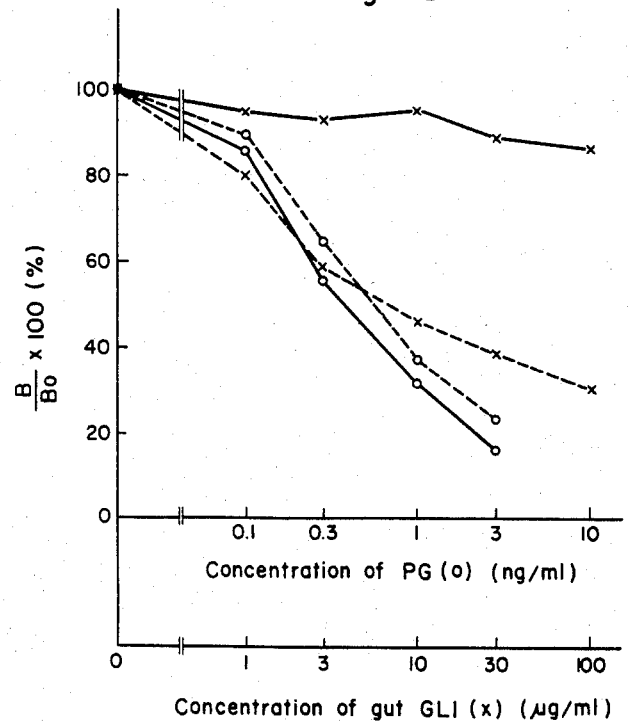

The results are shown in FIG. 8.

FIG. 8 shows the standard curves of PG (o) and gut GLI (x) in EIA using the anti-PG serum prepared in the above (1) and PG-labeling β-D-galactosidase conjugate ["Igakuno-Ayumi" (Progress in Medical Science), vol. 103 (1977), p. 25] (dotted line) and the specific anti-PG antibody prepared in Example 10 (2) and PG C-terminal peptide (21-29)-labeling β-D-galactosidase conjugate ("Journal of Biochemistry", vol. 86 (1979), p. 943) (solid line). These results indicate that the sensitivity of PG detection with the system employing the specific anti-PG antibody is higher than that with the system employing the anti-PG serum, and that whereas the anti-PG serum shows a strong cross-reactivity with gut GLI, the specific anti-PG antibody shows substantially no corss-reactivity with gut GLI.

TABLE 4

| Amino acid | The number of moles of each amino acid of antibody per 100 moles of glycine. |
|---|---|
| Lys | 98 |
| His | 40 |
| Arg | 42 |
| Asp | 112 |
| Thr | 101 |
| Ser | 132 |
| Glu | 140 |
| Pro | 107 |
| Gly | 100 |
| Ala | 77 |
| Val | 135 |
| Met | 3 |
| Ile | 33 |
| Leu | 111 |
| Tyr | 41 |
| Phe | 57 |

EXAMPLE 11

β-D-galactosidase (Boehringer-Manheim, West Germany) was dissolved in the following buffers (aqueous solutions) (a) and (b). The concentration of β-Gal in each solution was 500 ng/ml.

(a) 0.05 M Phosphate buffer (pH 7.0) containing 5 w/v % of sugar or sugar alcohol (the species of sugar and sugar alcohol are set forth in Table 5), 0.2% of bovine serum albumin and 0.001 M of $MgCl_2$.

(b) The buffer as above, except that neither sugar nor sugar alcohol was incorporated.

Each of the above β-Gal-containing aqueous compositions was frozen at −40° C. and, then, lyophilized at 10° C. and ≦10 mmHg to give a freeze-dried material. Each composition was allowed to stand at room temperature for 2 weeks, after which it was reconstituted and its β-Gal activity was measured (It was reacted with 4-methylumbelliferyl- β-D-galactopyranoside at 25° C. for 10 minutes). The results are given in Table 5.

TABLE 5

| Species of sugar and sugar alcohol | Enzymatic activity* |
|---|---|
| (a) Arabinose | 87 |
| Xylose | 79 |
| Xylitol | 79 |
| Ribose | 76 |
| Glucose | 86 |
| Sorbitol | 88 |
| Fructose | 84 |
| Mannose | 84 |
| Mannitol | 93 |
| Inositol | 95 |
| Rhamnose | 86 |
| Sucrose | 96 |
| Maltose | 83 |
| Cellobiose | 82 |
| Trehalose | 88 |
| Gentiobiose | 85 |
| Raffinose | 91 |
| Maltotriose | 82 |

TABLE 5-continued

| Species of sugar and sugar alcohol | Enzymatic activity* |
|---|---|
| (b) Not added | 8 |

*Relative values with initial activity taken as 100.

It will be apparent from the above results that compositions reconstituted from the lyophilizates of β-Gal-containing aqueous compositions (a) all show enzymatic activities not less than 76% of initial activity. On the other hand, the composition reconstituted from β-Gal-containing aqueous composition (b) has an enzymatic activity only as low as 8% of initial activity.

EXAMPLE 12

The pancreatic glucagon C-terminal fragment peptide (21-29)-β-Gal conjugate (European Patent Application Publication No. 9147) was dissolved in the following buffers (aqueous solutions) (a) and (b). The concentration of β-Gal in each solution was 100 ng/ml.

(a) 0.05 M Phosphate buffer (pH 7.0) containing 5 w/v% of sucrose, 0.2% of bovine serum albumin and 0.001 M of $MgCl_2$.

(b) The same buffer as above except that sugar was not contained.

Each of the above aqueous composition containing β-Gal was frozen at −40° C. and then lyophilized at 10° C. and ≦10 mmHg. The freeze-dried composition was purged well with nitrogen gas and sealed in a nitrogen atmosphere. This lyophilizate was stored at 10° C.

After 20 weeks the lyophilizate was unsealed. The enzymatic activity of the composition reconstituted from lyophilizate (a) was substantially the same as the initial activity A dilution (100 μl) of this liquid [which had a predetermined suitable enzymatic activity (ca. 10 μU/ml)] was admixed with 100 μl of a varying dilution of antiserum (N6E: European Patent Application Publication No. 9147), 50 μl of Antagosan (Hoechst, West Germany, 100 thousand units/ml), and 250 μl of assay buffer [0.02 M phosphate buffer (pH 7.3) containing 0.5% human serum albumin, 0.5% ethylenediamine tetraacetate disodium.$2H_2O$, 0.1% $NaN_3$ and 0.1 M NaCl]. The mixture was held at a temperature of 5° C. for 24×4 hours, whereby the enzymatic activity of the reconstituted β-D-galactosidase-containing aqueous composition was bound to the antiserum. Then, 100 μl of a 5% suspension of anti-rabbit IgG antibody-cellulose conjugate was added and the reaction was further conducted at 30° C. for 4 hours. This reaction mixture was centrifuged, the sediment was washed and suspended in 500 μl of a substrate solution [20 μg/ml of 4-methylumbelliferyl-β-D-galactopyranoside in 0.01 M phosphate buffer (pH 7.0) containing 0.1% bovine serum albumin, 0.1% $NaN_3$, 0.1 M NaCl and 1 mM $MgCl_2$]. The reaction was conducted at room temperature overnight. After this reaction, the fluorescence intensity of 4-methylumbelliferone liberated on enzymatic hydrolysis was measured at the excitation wavelength of 365 nm and the fluorescent wavelength of 450 nm.

The assay of pancreatic glucagon in the test fluid was performed as follows. The above predetermined dilution of antiserum (100 μl ) and the β-D-galactosidase-containing aqueous composition (100 μl) were added to a mixture of 50 μl of the test fluid, 50 μl of Antagosan and 200 μl of the assay buffer, and thereafter, the same procedure as described above followed to estimate the titer of PG.

Figure 9:
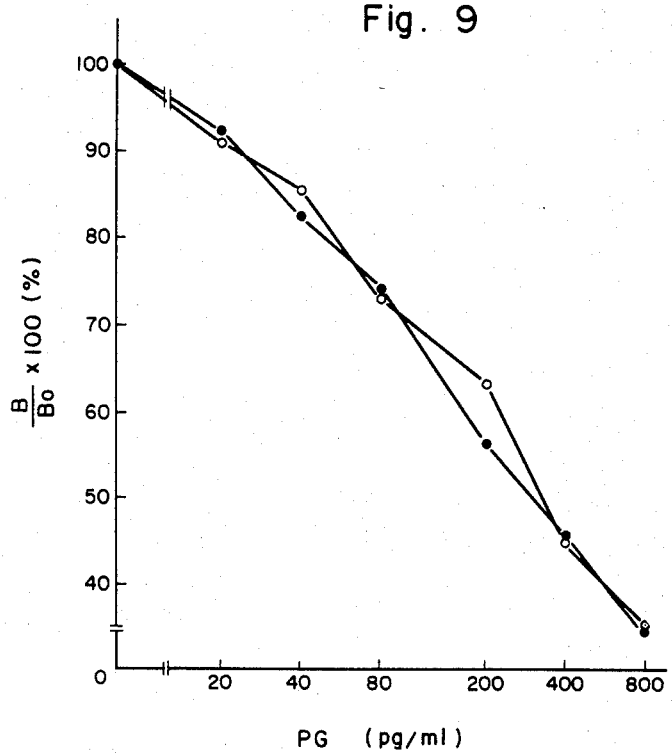

FIG. 9 shows the results of EIA by the competitive binding method described hereinbefore [In FIG. 9, -o- represents the results obtained with the composition unsealed from lyophilizate (a); -●- represents the results with the unlyophilized β-Gal-containing composition]. It will be apparent from FIG. 9 that the composition obtainable on unsealing of lyophilizate (a) gives results identical to those obtainable with the unlyophilized β-Gal-composition. The composition obtained on unsealing of lyophilizate (b) shows an enzymatic activity of no more than 0.1% of initial activity and cannot be used for EIA.

EXAMPLE 13

The conjugate of hCG-β-C-terminal fragment peptide (130–145)[peptide II] and β-Gal prepared in Example 3 was treated in the manner as Example 12 to prepare lyophilizates (a) and (b).

After 16 weeks the two lyophilizates were unsealed. The enzymatic activity of the composition obtained on unsealing of lyophilizate (a) was substantially equal to its initial activity. A predetermined dilution (100 μl) of this liquid [which had a predetermined suitable enzymatic activity (ca. 20 μU/ml)] was admixed with 100 μl of a varying dilution of antiserum (the specific anti-hCG antibody) and 300 μl of assay buffer [0.02 M phosphate buffer (pH 7.3) containing 0.5% human serum albumin, 0.5% ethylenediamine tetraacetate disodium.2H$_2$O, 0.1% NaN$_3$ and 0.1 M NaCl] and the mixture was allowed to stand at 5° C. for 48 hours, whereby the enzymatic activity of the β-D-galactosidase was bound to the antiserum. Then, 100 μl of a 2.5% suspension of anti-rabbit IgG antibody-cellulose conjugate was added and the reaction was further conducted at 20° C. for 4 hours. This mixture was centrifuged and the sediment was washed and suspended in 500 μl of a substrate solution [20 μg/ml of 4-methylumbelliferyl-β-D-galactopyranoside dissolved in 0.02 M phosphate buffer (pH 7.0) containing 0.1% bovine serum albumin, 0.1% NaN$_3$, 0.1 M NaCl and 1 mM MgCl$_2$]. The reaction was conducted at room temperature overnight. Then, the fluorescence intensity of 4-methylumbelliferone released on enzymatic hydrolysis was measured at the excitation wavelength of 365 nm and the fluorescent wavelength of 450 nm.

The titer of hCG in a test fluid was estimated in the following manner. The above predetermined antiserum dilution (100 μl) and the β-D-galactosidase-containing aqueous composition (100 μl) were added to a mixture of 50 μl of the test fluid and 250 μl of assay buffer and the same assay procedure as described hereinbefore was carried out.

Figure 10:
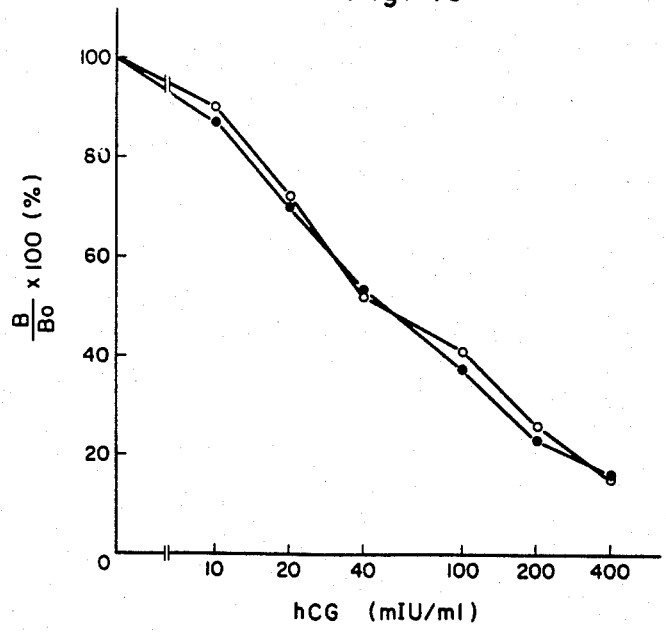

FIG. 10 shows the results of EIA run by said competitive binding method. (In FIG. 10, -o- represents the results obtained with the composition reconstituted from lyophilizate (a) and -●- represents the results with the unlyophilized β-Gal-containing aqueous composition.) It will be apparent that the composition from lyophilizate (a) produces results comparable with those obtainable with the unlyophilized β-Gal-containing aqueous composition. The composition reconstituted from lyophilizate (b) shows an enzymatic activity equivalent to no more than 10% of initial activity and cannot be utilized for EIA.

EXAMPLE 14

The hCG-β-Gal conjugate prepared in Reference Example 5 was treated in the manner as Example 12 to give lyophilizates (a) and (b).

After 20 weeks, each lyophilizate was reconstituted. The enzymatic activity of the composition from lyophilizate (a) was not much different from the initial value.

Figure 11:
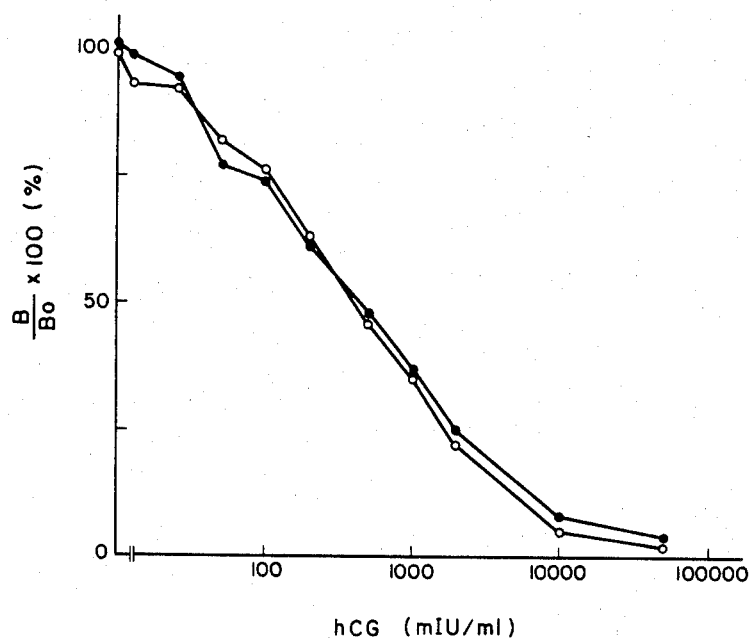

FIG. 11 shows the results of hCG measured by EIA in the competitive binding system (In FIG. 11, -o- represents results with the composition from lyophilizate (a) and -●- represents results β-Gal-containing aqeuous composition.). It will thus be apparent from FIG. 11 that the composition reconstituted from lyophilizate (a) yields assay results identical to those obtainable with the unlyophilized β-Gal-containing composition. The composition from lyophilizate (b) has an enzymatic activity of no more than 10% of initial activity and cannot be utilized for EIA.

EXAMPLE 15

The conjugate of β-adrenergic drug (trans-5-hydroxymethyl-6-hydroxy-2-isopropylamino-1,2,3,4-tetrahydronaphthalene-1-ol) and β-Gal [Immunopharmacology, Vol. 1, page 3 (1979)] was treated in the manner as Example 12 to give lyophilizates (a) and (b).

After 12 weeks, each of the lyophilizates was reconstituted. The enzymatic activity of the composition from lyophilizate (a) was substantially equal to initial activity.

Figure 12:
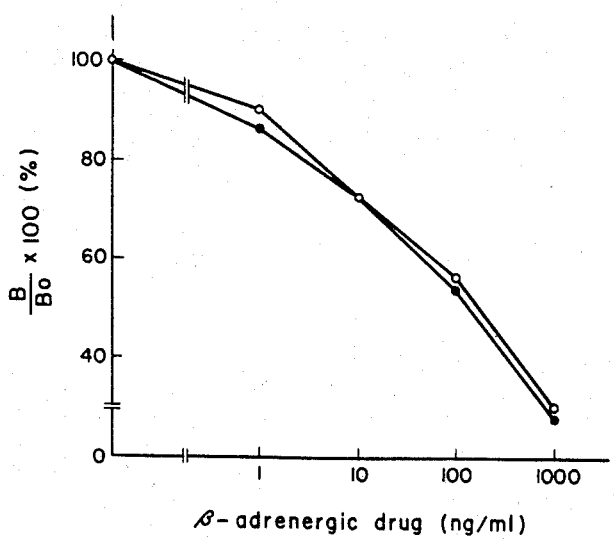

FIG. 12 shows results of the EIA of the β-adrenergic drug by the competitive binding method described in Example 13 [In FIG. 12, -o- represents the results obtained with the composition from lyophilizate (a) and -●- represents the results obtained with the unlyophilized β-Gal containing aqueous composition.]. The composition from lyophilizate (a) gave results identical to those obtainable with the unlyophilized β-Gal-containing aqueous composition. The composition from lyophilizate (b) had an enzymatic activity as low as no more than 10% of initial activity and cannot be utilized for EIA.

EXAMPLE 16

The anti-hCG antibody-β-Gal conjugate prepared in Reference Example 6 was treated in the manner as Example 12 to give lyophilizates (a) and (b).

After 23 weeks, these lyophilizates were reconstituted. The enzymatic activity of the composition from liophilizate (a) was substantially not different from the initial value.

EXAMPLE 17

A conjugate of anti-human IgG antibody [Miles Laboratories, U.S.A.] and β-Gal [Journal of Immunology 116, 1554 (1976)] was treated in the manner as Example 12 to give lyophilizates (a) and (b).

After 12 weeks, the above lyophilizates were reconstituted. The enzymatic activity of the composition from lyophilizate (a) was substantially unchanged from the initial value.

EXAMPLE 18

The conjugate of anti-hCG antibody and β-Gal according to Reference Example 6 was treated in the manner as Example 12 except that 5% (w/v) sucrose in buffer (a) was replaced with 3% (w/v) lactose or galactose to give lyophilizates (a) and (b).

After 23 weeks, the lyophilizates were reconstituted. The enzymatic activity of the composition from the lactose- or galactose-containing lyophilizate (a) showed no change at all.

EXAMPLE 19

The concentration of hCG in the urine or serum of a normal person and of a pregnant woman was measured by the following procedure using the hCG enzyme immunoassay kit described below. The results are shown in Table 6. The hCG enzyme immunoassay kit:

(1) The portion of the specific anti-human chorionic gonadotropin antibody obtained in Example 1 which binds about 40% of the enzymatic activity of the peptide (I)-$\beta$-D-galactosidase conjugate added to the reaction system.

(2) The portion of the peptide(II) -$\beta$-D-galactosidase conjugate which has an enzymatic activity of about 0.4 $\mu$U.

(3) From 0 to 100 IU of standard human chorionic gonadotropin.

(4) 0.02 M phosphate buffer containing 0.15 M NaCl, 0.5% human serum albumin, 0.5% EDTA and 0.1% NaN$_3$ which is used for diluting the above reagents (1) to (3) and test fluid.

(5) A 2.5 (w/v) % suspension of anti-rabbit IgG-cellulose complex.

(6) 10 $\mu$g of 4-methylumbellifery-$\beta$-D-galactoside.

(7) 0.02 M Phosphate buffer (pH 7.0) containing 0.1 M NaCl, 1 mM MgCl$_2$, 0.1% bovine serum albumin and 0.1% NaN$_3$ which is used for washing the cellulose (5) and for dissolving the substrate (6).

(8) 0.1 M Carbonate buffer, pH 10.5.

Procedure

To 100 $\mu$l of reagent (1) was added 250 $\mu$l of reagent (4) and 50 $\mu$l of either standard human chorionic gonadotropin or the sample to be tested, followed by addition of 100 $\mu$l of reagent (2). The mixture was reacted at 4° C. for 40 hours. Then, 100 $\mu$l of reagent suspension (5) was added and after thorough stirring, the reaction was further conducted at 20° C. for 4 hours. The cellulose was then washed with reagent (7) and, then, 500 $\mu$l of reagent (6) was added so as to initiate the enzymatic reaction. This reaction was conducted at 20° C. for 16 hours, at the end of which time the reaction was terminated with 3 ml of reagent (8). The intensity of fluorescence of the reaction system was measured to estimate the concentration of human chorionic gonadotropin in the test fluid.

TABLE 6

| Test sample | | Titer of hCG (mIU/ml) |
|---|---|---|
| Normal human urine | 1 | 26 |
| | 2 | <3 |
| Urine of pregnant woman | 1 | 2,800 |
| | 2 | >100,000 |
| Normal human serum | 1 | 16 |
| | 2 | <3 |
| | 3 | 4 |
| | 4 | <3 |
| | 5 | 11 |
| Serum of pregnant woman | 1 | 28,000 |
| | 2 | 18,800 |
| | 3 | 49,200 |
| Serum of woman given pergonal menotropins and hCG | 1 | 210 |
| | 2 | 350 |
| | 3 | 250 |

TABLE 6-continued

| Test sample | | Titer of hCG (mIU/ml) |
|---|---|---|
| | 4 | 80 |
| | 5 | 40 |
| | 6 | 92 |
| | 7 | 400 |
| | 8 | 325 |
| Serum of pregnant woman in the early stage | 1 | 195 |
| | 2 | 130 |
| | 3 | 115 |
| | 4 | 270 |
| | 5 | 280 |

EXAMPLE 20

The concentration of hCG in the urine or serum of a normal person and of a pregnant woman was measured by the following procedure using the hCG enzyme immunoassay kit described below. The results are shown in Table 7. The hCG enzyme immunoassay kit:

(1) The portion of the specific anti-human chorionic gonadotropin antibody obtained in Example 1 which binds about 40% of the enzymatic activity of the peptide(I)-$\beta$-D-galactosidase conjugate added to the reaction system.

(2) The portion of the lyophilizate of the peptide (II)-$\beta$-D-galactosidase conjugate obtained in Example 13 which has an enzymatic activity of about 0.4 $\mu$U.

(3) From 0 to 100 IU of standard human chorionic gonadotropin.

(4) 0.02 M phosphate buffer containing 0.15 M NaCl, 0.5% human serum albumin, 0.5% EDTA and 0.1% NaN$_3$ which is used for diluting the above reagents (1) to (3) and test fluid.

(5) A 2.5 (w/v) % suspension of anti-rabbit IgG-cellulose complex.

(6) 10 $\mu$g of 4-methylumbelliferyl-$\beta$-D-galactoside.

(7) 0.02 M Phosphate buffer (pH 7.0) containing 0.1 M NaCl, 1 mM MgCl$_2$, 0.1% bovine serum albumin and 0.1% NaN$_3$ which is used for washing the cellulose (5) and for dissolving the substrate (6).

(8) 0.1 M Carbonate buffer, pH 10.5.

The EIA procedure was conducted in accordance with the procedure of Exmaple 19.

TABLE 7

| Test sample | | Titer of hCG (mIU/ml) |
|---|---|---|
| Normal human urine | 1 | 26 |
| | 2 | <3 |
| Urine of pregnant woman | 1 | 2,800 |
| | 2 | >100,000 |
| Normal human serum | 1 | 16 |
| | 2 | <3 |
| | 3 | 4 |
| | 4 | <3 |
| | 5 | 11 |
| Serum of pregnant woman | 1 | 28,000 |
| | 2 | 18,800 |
| | 3 | 49,200 |
| Serum of pregnant woman in the early stage | 1 | 61 |
| | 2 | 54 |
| | 3 | 285 |
| | 4 | 185 |
| | 5 | 76 |
| Serum of mole-extracted woman | 1 | 54 |
| | 2 | 80 |
| | 3 | 41 |
| | 4 | 100 |
| | 5 | 265 |

What we claim is:

1. An enzyme immunoassay method involving the use of an antibody as a reagent, which comprises using an antibody obtained by inoculating human chorionic gonadotropin into an animal to produce an anti-human chorionic gonadotropin antibody, contacting a body fluid containing the anti-human chorionic gonadotropin antibody thus produced with a peptide of the formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$, wherein said peptide is synthetically prepared by chemically combining at least one member selected from the group consisting of amino acids and peptide fragments of fewer amino acids than said peptide, said peptide being insolubilized on a carrier, and eluting the anti-human chorionic gonadotropin antibody thus specifically absorbed.

2. A method as claimed in claim 1, wherein the peptide is H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH.

3. An assay kit for the kit for the detection of human chorionic gonadotropin, which comprises:

(1) A portion of a peptide-$\beta$-D-galactosidase conjugate which has an enzymatic activity of about 0.1 to 500 $\mu$U, the conjugate being prepared by coupling $\beta$-D-galactosidase with a peptide of the formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$;

(2) A portion of anti-human chorionic gonadotropin antibody which binds about 5 to 100% of the enzymatic activity of the conjugate, the antibody being produced by contacting a peptide of the formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$, wherein said peptide is synthetically prepared by chemically combining at least one member selected from the group consisting of amino acids and peptide fragments of fewer amino acids than said peptide, said peptide being insolubilized on a carrier, with a body fluid containing an antibody reactive to human chorionic gonadotropin, and then eluting the thus-specifically absorbed antibody;

(3) From 0 to 500 Iu of standard human chorionic gonadotropin;

(4) A buffer solution which is used for diluting the above reagents (1) to (3) and the sample fluid to be assayed;

(5) A given amount of an insoluble anti-animal IgG-carrier conjugate which is sufficient to bind all of first antibody (2);

(6) From about 1 to 100 $\mu$G of a substrate;

(7) A buffer solution for washing the second antibody-carrier conjugate (5) and dissolving the substrate (6); and (8) A buffer solution for terminating the enzymatic reaction.

4. In a method for enzyme immunoassay of human chorionic gonadotropin involving the use of a peptide-enzyme conjugate as an assay reagent, an improvement which comprises using a peptide-enzyme conjugate prepared by coupling a labeling enzyme with a peptide of the general formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of the peptide Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$, and an antibody obtained by inoculating human chorionic gonadotropin into an animal to produce an anti-human chorionic gonadotropin antibody, contacting a body fluid containing the anti-human chorionic gonadotropin antibody thus produced with a peptide of the formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$, wherein said peptide is synthetically prepared by chemically combining at least one member selected from the group consisting of amino acids and peptide fragments of fewer amino acids than said peptide, said peptide being insolubilized on a carrier, and eluting the anti-human chorionic gonadotropin antibody thus specifically absorbed.

5. The improvement as claimed in claim 4, wherein R$_1$ is a peptide fragment selected from the group consisting of Ala-Pro-Pro-Pro-Ser-Leu-Pro-Ser-Pro-Ser-Arg-Leu-Pro-Gly, Ser-Pro-Ser-Arg-Leu-Pro-Gly and Gly.

6. The improvement as claimed in claim 4, wherein the labeling enzyme is a glycosidase or phosphatase.

7. The improvement as claimed in claim 4, wherein the labeling enzyme is $\beta$-galactosidase or alkaline phosphatase.

8. The improvement as claimed in claim 4, wherein the peptide-enzyme conjugate is a freeze-dried peptide-$\beta$-D-galactosidase conjugate.

9. A method for producing a specific antibody, which comprises inoculating human chorionic gonadotropin into an animal to produce an anti-human chorionic gonadotropin antibody, contacting a body fluid containing the anti-human chorionic gonadotropin antibody thus produced with a peptide of the formula:

H-R$_1$-Pro-Ser-Asp-Thr-Pro-Ile-Leu-Pro-Gln-OH wherein R$_1$ is a peptide fragment consisting of 1 to 14 amino acid residues including Gly in the 14-position of Ala$^1$-Pro$^2$-Pro$^3$-Pro$^4$-Ser$^5$-Leu$^6$-Pro$^7$-Ser$^8$-Pro$^9$-Ser$^{10}$-Arg$^{11}$-Leu$^{12}$-Pro$^{13}$-Gly$^{14}$, wherein said peptide is synthetically prepared by chemically combining at least one member selected from the group consisting of amino acids and peptide fragments of fewer amino acids than said peptide, said peptide being insolubilized on a carrier, and eluting the anti-human chorionic gonadotropin antibody thus specifically absorbed.

10. A method as claimed in claim 9, wherein the peptide is H-Ala-Pro-Pro-Pro-Ser-Leu-Pro-Ser-Pro-Ser-Arg-Leu-Pro-Gly-Pro-Ser-Asp-Thr-Pro-Ile-Leu-Pro-Gln-OH.

* * * * *